United States Patent
Zhang

(10) Patent No.: US 7,309,709 B2
(45) Date of Patent: Dec. 18, 2007

(54) THIAZOLE SULFONAMIDE COMPOUNDS FOR THE TREATMENT OF NEURODEGENERATIVE DISORDERS

(75) Inventor: Lei Zhang, Groton, CT (US)

(73) Assignee: Pfizer Inc., New York, NY (US)

( * ) Notice: Subject to any disclaimer, the term of this patent is extended or adjusted under 35 U.S.C. 154(b) by 456 days.

(21) Appl. No.: 11/078,741

(22) Filed: Mar. 11, 2005

(65) Prior Publication Data

US 2005/0222223 A1    Oct. 6, 2005

Related U.S. Application Data

(60) Provisional application No. 60/558,627, filed on Apr. 1, 2004.

(51) Int. Cl.
*A61K 31/426* (2006.01)
*A61K 31/445* (2006.01)
*C07D 277/20* (2006.01)
*C07D 417/02* (2006.01)

(52) U.S. Cl. ............... 514/326; 546/184; 546/192; 546/207; 546/209; 548/146; 548/202; 548/203; 548/204; 514/315; 514/317; 514/365

(58) Field of Classification Search ............... 546/184, 546/192, 207; 548/146, 202, 203, 204; 514/315, 514/317, 326, 365
See application file for complete search history.

(56) References Cited

U.S. PATENT DOCUMENTS 6,306,887 B1   10/2001   Chupak et al.

*Primary Examiner*—Golam M. M. Shameem
(74) *Attorney, Agent, or Firm*—Jeffrey H. Tidwell; Bryan C. Zielinski

(57) ABSTRACT

The present invention relates to compounds of the Formula:

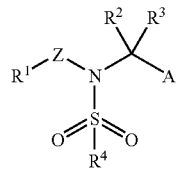

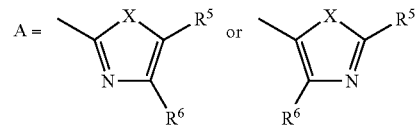

wherein $R^1$ to $R^6$, X, Z and A are as defined. These compounds have activity inhibiting production of Aβ-peptide. The invention also relates to pharmaceutical compositions and methods for treating diseases, for example, neurodegenerative diseases, e.g., Alzheimer's disease, in a mammal comprising compounds of the present Formula.

13 Claims, No Drawings

THIAZOLE SULFONAMIDE COMPOUNDS FOR THE TREATMENT OF NEURODEGENERATIVE DISORDERS

CROSS REFERENCE TO RELATED APPLICATION

The present application claims benefit of U.S. Ser. No. 60/558,627 filed on Apr. 1, 2004, which is incorporated by reference herein in its entirety.

FIELD OF THE INVENTION

The present invention relates to the treatment of neurodegenerative and/or neurological disorders such as Alzheimer's disease in mammals, including humans. This invention also relates to inhibiting, in mammals, including humans, the production of Aβ-peptides that can contribute to the formation of neurological deposits of amyloid protein. More particularly, this invention relates to thiazole sulfonamide compounds useful, e.g., for the treatment of neurodegenerative and/or neurological disorders, such as Alzheimer's disease, related to Aβ-peptide production.

BACKGROUND OF THE INVENTION

Dementia results from a wide variety of distinctive pathological processes. The most common pathological processes causing dementia are Alzheimer's disease (AD), cerebral amyloid angiopathy (CAA) and prion-mediated diseases (see, e.g., Haan et al. *Clin. Neurol Neurosurg.* 1990, 92(4): 305-310; Glenner et al. *J. Neurol. Sci.* 1989, 94:1-28). AD affects nearly half of all people past the age of 85, the most rapidly growing portion of the United States population. As such, the number of AD patients in the United States is expected to increase from about 4 million to about 14 million by the middle of the next century. Treatment of AD typically is the support provided by a family member in attendance. Stimulated memory exercises on a regular basis have been shown to slow, but not stop, memory loss. A few drugs, for example Aricept™, provide treatment of AD.

A hallmark of AD is the accumulation in the brain of extracellular insoluble deposits called amyloid plaques and abnormal lesions within neuronal cells called neurofibrillary tangles. Increased plaque formation is associated with an increased risk of AD. Indeed, the presence of amyloid plaques, together with neurofibrillary tangles, is the basis for definitive pathological diagnosis of AD.

The major components of amyloid plaques are the amyloid Aβ-peptides, also called Aβ-peptides, that consist of several proteins including 38, 40, 42 or 43 amino acids, designated as the $A\beta_{1-38}$, $A\beta_{1-40}$, $A\beta_{1-42}$ and $A\beta_{1-43}$ peptides, respectively. The Aβ-peptides are thought to cause nerve cell destruction, in part, because they are toxic to neurons in vitro and in vivo.

The Aβ peptides are derived from larger amyloid precursor proteins (APP proteins), that consist of four proteins containing 695, 714, 751 or 771 amino acids, designated as the $APP_{695}$, $APP_{714}$, $APP_{751}$, and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. The secretase that forms the amino terminal end of the Aβ-peptides is called the beta-secretase. The secretase that forms the carboxyl terminal end of the Aβ-peptides is called the gamma-secretase (Haass, C. and Selkoe, D. J. 1993 *Cell* 75:1039-1042).

This invention relates to novel thiazole sulfonamide compounds that inhibit Aβ-peptide production, to pharmaceutical compositions comprising such compounds, and to methods of using such compounds to treat neurodegenerative and/or neurological disorders.

SUMMARY OF THE INVENTION

The present invention relates to compounds of the Formula I:

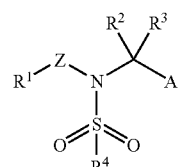

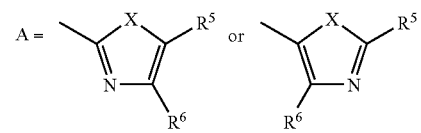

wherein:

1) $R^1$ is $-(C_6-C_{14})$ aryl, or $-(5-14$ membered$)$ heteroaryl, wherein said aryl and heteroaryl are each optionally substituted with one or more $(C_0-C_4$ alkylene$)$-$R^{13}$;

2) $R^2$ and $R^3$ are independently selected from the group consisting of:

—H, a straight or branched $C_1-C_6$ alkyl, $C_2-C_6$ alkenyl, $C_2-C_6$ alkynyl, $C_3-C_8$ cycloalkyl, $C_6-C_{14}$ aryl and (5-14 membered) heteroaryl, wherein said alkyl, alkenyl and alkynyl are each optionally substituted with substituents selected from the group consisting of —F, —Cl, —Br, —OH, $C_1-C_4$ alkoxy, and —S—$(C_1-C_4)$alkyl, and wherein said aryl and heteroaryl are each optionally substituted with one or more $(C_0-C_4$ alkylene$)$-$R^{13}$; or $R_2$ and $R_3$ taken together form a $C_3-C_8$ cycloalkyl;

3) $R^4$ is $C_6-C_{14}$ aryl or (5-14 membered) heteroaryl substituted with one or more $(C_0-C_4$ alkylene$)$-$R^{13}$;

4) $R^5$ and $R^6$ are independently selected from the group consisting of:

—H, —F, —Cl, —Br, —CN, —$NO_2$, —CHO, —C(=O)$NR^9R^{10}$, —C(=O)$OR^{10}$, —$NR^9R^{10}$, —$NR^9C(=O)R^{10}$,

—$NR^9C(=O)OR^{10}$, and $NR^9C(=O)NR^9R^{10}$; or $R^5$ and $R^6$ are independently a straight or branched $C_1-C_{20}$ alkyl, $C_2-C_{20}$ alkenyl, $C_2-C_{20}$ alkynyl, $(C_0-C_6$ alkylene$)$-$(C_3-C_{12}$ cycloalkyl), or $(C_0-C_6$ alkylene$)$-$(C_3-C_{12}$ heterocycloalkyl), wherein said alkyl, alkenyl, alkynyl, alkylene, cycloalkyl and heteroalkyl are each optionally substituted with one or more $(C_0-C_6$ alkylene$)$-$R^7$; or $R^5$ and $R^6$ are independently selected from $(C_0-C_6$ alkylene$)$-$(C_6-C_{14}$ aryl), or $(C_0-C_6$ alkylene$)$-(5-14 membered heteroaryl), wherein said aryl and heteroaryl are each optionally substituted with one or more $R^7$ and wherein said alkylene is optionally substituted with one or more $(C_0-C_6$ alkylene$)$-$R^8$; or $R^5$ and $R^6$ when attached to the adjacent carbon atoms of the thiazole ring, together form a (4-8 membered) cycloalkyl, (4-8 membered) heterocycloalkyl, or $C_6-C_{10}$ aryl wherein said cycloalkyl or, heterocycloalkyl are each substituted with one or more ($C_0$-$C_6$ alkylene)-$R^8$, ($C_0$-$C_6$ alkylene)-($C_6$-$C_{14}$ aryl), or ($C_0$-$C_6$ alkylene)-(5-14 membered heteroaryl) and wherein said aryl and heteroaryl are each optionally substituted with one or more $R^7$.

5) Z is a bond or a straight or branched $C_1$-$C_6$ alkylene, wherein each hydrogen atom of said alkylene is optionally independently replaced with a fluorine.

6) $R^7$ is —F, —Cl, —Br, —OH, —CN, —CHO, —NO$_2$, —NR$^9$R$^{10}$, —NR$^9$C(=O)R$^{10}$, —NR$^9$C(=O)NR$^9$R$^{10}$, —NR$^9$C(=O)OR$^{10}$, —OC(=O)—R$^9$, —OC(=O)NR$^9$R$^{10}$, —C(=O)NR$^9$R$^{10}$, —C(=O)OR$^{10}$, —SO$_2$NR$^9$R$^{10}$, —$C_1$-$C_6$ alkyl, —$C_2$-$C_6$ alkenyl, —$C_2$-$C_6$ alkynyl, —$C_3$-$C_8$ cycloalkyl, —$C_3$-$C_8$ heterocycloalkyl, —$C_1$-$C_6$ alkoxy, -($C_6$-$C_{14}$) aryloxy, -(5-14 membered) heteroaryloxy, -($C_0$-$C_4$ alkylene)-($C_6$-$C_{14}$) aryl, or -($C_0$-$C_4$ alkylene)-(5-14 membered) heteroaryl, wherein said alkyl, alkenyl, alkynyl, cycloalkyl and heterocycloalkyl are each optionally substituted with one or more $R^8$, and wherein each hydrogen atom of said alkyl, alkenyl, alkynyl, cycloalkyl, heterocycloalkyl and alkoxy is optionally independently replaced with a fluorine;

7) $R^8$ is —F, —Cl, —Br, —CN, —CHO, —OR$^9$, —OC(=O)—R$^9$, —OC(=O)NR$^9$R$^{10}$, —NO$_2$, —NR$^9$R$^{10}$, —NR$^9$C(=O)R$^{10}$, —NR$^9$C(=O)NR$^9$R$^{10}$, —NR$^9$C(=O)OR$^{10}$, —C(=O)NR$^9$R$^{10}$, —SO$_2$NR$^9$R$^{10}$, —C(=O)R$^{10}$, or —C(=O)OR$^{10}$.

8) $R^9$ and $R^{10}$ are —H, —$C_1$-$C_6$ alkyl, —$C_2$-$C_6$ alkenyl, —$C_2$-$C_6$ alkynyl, -($C_0$-$C_4$ alkylene)-($C_3$-$C_8$ cycloalkyl), -($C_0$-$C_4$ alkylene)-($C_6$-$C_{14}$ aryl), -($C_0$-$C_4$ alkylene)-(3-8 membered heterocycloalkyl), or -($C_0$-$C_4$ alkylene)-(5-14 membered heteroaryl), wherein said alkyl, alkenyl, alkynyl, cycloalkyl, aryl, heterocycloalkyl, and heteroaryl are each optionally independently substituted with from one or more substituents independently selected from the group consisting of —F, —Cl, —Br, —CN, —OH, —NO$_2$, —NR$^{11}$R$^{12}$, —C(=)ONR$^{11}$R$^{12}$, —C(=O)R$^{11}$, —C(=O)OR$^{12}$, —SO$_2$NR$^{11}$R$^{12}$, —$C_1$-$C_6$ alkyl, —$C_1$-$C_6$ alkoxy, —$C_1$-$C_6$ hydroxyalkyl, -($C_0$-$C_4$)-($C_6$-$C_{14}$) aryl), and -($C_0$-$C_4$)-(5-14 membered heteroaryl).

Or $R^9$ and $R^{10}$ with nitrogen forms a 4-8 membered heterocycloalkyl moiety, wherein said heterocycloalkyl is optionally substituted with one or more substituents selected from the group consisting of —F, —Cl, —Br, —CN, —CHO, —OH, —NO$_2$, —NR$^{11}$R$^{12}$, —C(=)ONR$^{11}$R$^{12}$, —C(=O)R$^{11}$, —C(=O)OR$^{12}$, —SO$_2$NR$^{11}$R$^{12}$, 13 $C_1$-$C_6$ alkyl, —$C_2$-$C_6$ alkenyl, —$C_2$-$C_6$ alkynyl, —$C_1$-$C_6$ alkoxy, —$C_3$-$C_8$ cycloalkyl, $C_3$-$C_8$ heterocycloalkyl, $C_6$-$C_{10}$ aryl, and 5-14 membered heteroaryl, wherein said alkyl, alkenyl, alkynyl, alkoxy, cycloalkyl, heterocycloalkyl, aryl, heteroaryl are each optionally substituted with F, —Cl, —Br, —CN, —OR$_{11}$, —OC(=O)—R$^{11}$, —OC(=O)NR$^{11}$R$^{12}$, —NO$_2$, —NR$^{11}$R$^{12}$, —NR$^{11}$C(=O)R$^{12}$, —NR$^{11}$C(=O)NR$^{11}$R$^{12}$, —NR$^{11}$C(=O)OR$^{12}$, —C(=O)NR$^{11}$R$^{12}$, —SO$_2$NR$^{11}$R$^{12}$, —C(=O)R$^{11}$, or —C(=O)OR$^{11}$.

9) $R^{11}$ and $R^{12}$ are hydrogen, $C_1$-$C_6$ alkyl, $C_2$-$C_6$ alkenyl, $C_2$-$C_6$ alkynyl, $C_3$-$C_8$ cycloalkyl, 4-8 membered heterocycloalkyl, $C_6$-$C_{14}$ aryl or 5-14 membered heteroaryl, wherein said alkyl, alkenyl, alkynyl, aryl and heteroaryl are each optionally independently substituted with from one to three substituents independently selected from the group consisting of —OH, —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —NO$_2$, —CF$_3$, —NH$_2$, —NH($C_1$-$C_6$ alkyl), —N($C_1$-$C_6$ alkyl)$_2$, —C(=O)NH$_2$, —C(=O)NH($C_1$-$C_6$ alkyl), —C(=O)N($C_1$-$C_6$ alkyl)$_2$, —SO$_2$NH$_2$, —SO$_2$NH($C_1$-$C_6$ alkyl), —SO$_2$N($C_1$-$C_6$ alkyl)$_2$, —C(=O)H, —C(=O)OH and —C(=O)O($C_1$-$C_6$ alkyl), wherein said alkyl, alkenyl and alkynyl substituents are each optionally independently further substituted with from one to six fluorine atom;

Or $R^{11}$ and $R^{12}$ with nitrogen taken together to form a 4-8 membered heterocycloalkyl, wherein said heterocycloalkyl is optionally independently substituted with from one to three substituents independently selected from the group consisting of —OH, —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —NO$_2$, —CF$_3$, —NH$_2$, —NH($C_1$-$C_6$ alkyl), —N($C_1$-$C_6$ alkyl)$_2$, —C(=O)NH$_2$, —C(=O)NH($C_1$-$C_6$ alkyl), —C(=O)N($C_1$-$C_6$ alkyl)$_2$, —SO$_2$NH$_2$, —SO$_2$NH($C_1$-$C_6$ alkyl), —SO$_2$N($C_1$-$C_6$ alkyl)$_2$, —C(=O)H, —C(=O)OH and —C(=O)O($C_1$-$C_6$ alkyl), wherein said alkyl, alkenyl and alkynyl substituents are each optionally independently further substituted with from one to six fluorine atoms.

10) R is —F, —Cl, —Br, —CN, —CHO, —OH, —NO$_2$, —NR$_{11}$R$_{12}$, —C(=)ONR$^{11}$R$^{12}$, —C(=O)R$^{11}$, —C(=O)OR$^{12}$, —SO$_2$NR$^{11}$R$^{12}$, —$C_1$-$C_6$ alkyl, —$C_1$-$C_6$ alkoxy, —$C_3$-$C_8$ cycloalkyl, 4-8 membered heterocycloalkyl, $C_6$-$C_{10}$ aryl or 5-14 membered heteroaryl, wherein each hydrogen atom of said alkyl, alkoxy, cycloalkyl and heterocycloalkyl is optionally independently replaced with a fluorine;

11) X is S or O.

DETAILED DESCRIPTION OF THE INVENTION

The present invention is directed to compounds having the structural Formula I where the radicals have the meanings given above.

The term "halogen" or "halo," as used herein, unless otherwise indicated, includes F, Cl, Br, and I.

The term "alkyl", as used herein, unless otherwise indicated, includes saturated monovalent hydrocarbon radicals having straight or branched moieties. Examples of alkyl groups include, but are not limited to, methyl, ethyl, n-propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

Unless otherwise indicated, as used herein, the term "alkylene" includes saturated, divalent hydrocarbon radicals i.e., generally present as a bridging group between two other groups, having straight or branched moieties. Examples of alkylene groups include —CH$_2$-(methylene); —CH$_2$CH$_2$-(ethylene); —CH$_2$CH$_2$CH$_2$-(propylene), —CH(CH$_3$)CH$_2$-(isopropylene) etc.

The term "cycloalkyl", as used herein, unless otherwise indicated, includes non-aromatic saturated cyclic alkyl moieties consisting of one or more rings, wherein said rings (if more than one) share at least one carbon atom, wherein alkyl is as defined above. Examples of cycloalkyl include, but are not limited to, cyclopropyl, cyclobutyl, cyclopentyl, cyclohexyl, cycloheptyl, bicyclo-[3.1.0]-hexyl, bicyclo-[2.2.1]-hept-1-yl, norbornyl, spiro[4.5]decyl, spiro[4.4]nonyl, spiro[4.3]octyl, spiro[4.2]heptyl and adamantanyl.

The term "aryl", as used herein, unless otherwise indicated, includes an organic radical derived from an aromatic hydrocarbon by removal of one hydrogen, such as phenyl, naphthyl, indenyl, indanyl, and fluorenyl. "Aryl" encompasses fused ring groups wherein at least one ring is aromatic.

The terms "heterocyclic", "heterocycloalkyl", and like terms, as used herein, refer to non-aromatic cyclic groups consisting of one or more rings, wherein said rings (if more than one) share one or two atoms and each ring contains up to four heteroatoms (i.e. from zero to four heteroatoms, provided that at least one ring contains at least one heteroatom). The heterocyclic groups of this invention can also include ring systems substituted with one or more O, $S(O)_{zero-2}$, and/or N—$R^9$ as heteroatoms, wherein $R^9$ is as defined above, and wherein the subscript "zero-2" of $S(O)_{zero-2}$ represents a group of integers consisting of zero, 1, and 2. Thus, $S(O)_{zero-2}$ represents the group consisting of S, S(=O), and $S(O)_2$. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

The terms "heteroaryl", as used herein, refers to aromatic groups containing one or more heteroatoms (O, S, or N), preferably from one to four heteroatoms. A multicyclic group containing one or more heteroatoms wherein at least one ring of the group is a "heteroaryl" group. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

Compounds of the Formula I may have optical centers and therefore may occur in different enantiomeric and diastereomeric configurations. The present invention includes all enantiomers, diastereomers, and other stereoisomers of such compounds of the Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see Crystals and the Polarizing Microscope by N. H. Hartshorne and A. Stuart, 4$^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

As appreciated by the artisan, the use of Formula I is a convenience, and the invention is understood to envision and embrace each and every species thereunder as though individually identified and set forth herein. Thus, the present invention contemplates each species separately and any and all combinations and permutations of species falling within Formula I.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

In one aspect, Z is a bond.

In another aspect, Z is methylene.

In another aspect, R$^2$ is hydrogen and R$^3$ is independently selected from the group consisting of —H, a straight or branched C$_1$-C$_6$ alkyl, C$_2$-C$_6$ alkenyl, C$_2$-C$_6$ alkynyl, C$_6$-C$_{14}$ aryl and (5-14 membered) heteroaryl.

In another aspect, X is S.

In another aspect,

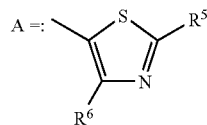

In another aspect,

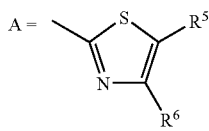

In another aspect, R$^6$ is —H, —F, —Cl, —CN, —CHO, a straight or branched C$_1$-C$_{10}$ alkyl, C$_2$-C$_{10}$ alkenyl, C$_2$-C$_{10}$ alkynyl, (C$_0$-C$_6$ alkylene)-(C$_3$-C$_{12}$ cycloalkyl), (C$_0$-C$_6$ alkylene)-(C$_3$-C$_{12}$ heterocycloalkyl), (C$_0$-C$_6$ alkylene)-(C$_6$-C$_{14}$ aryl), or (C$_0$-C$_6$ alkylene)-(5-14 membered heteroaryl), wherein said alkyl, alkenyl, alkynyl, alkylene, cycloalkyl and heteroalkyl are each optionally substituted with one or more (C$_0$-C$_6$ alkylene)-R$^7$; and wherein said aryl and heteroaryl are each optionally substituted with one or more R$^7$.

In another aspect, R$^5$ is independently selected from the group consisting of: —H, —F, —Cl, —Br, —CN, —CHO, —NO$_2$, —C(=O)NR$^9$R$^{10}$, —C(=O)OR$^{10}$, —NR$^9$R$^{10}$, —NR$^9$C(=O)R$^{10}$, —NR$^9$C(=O)OR$^{10}$, and NR$^9$C(=O)NR$^9$R$^{10}$;

or R$^5$ is straight or branched C$_1$-C$_{20}$ alkyl, C$_2$-C$_{20}$ alkenyl, C$_2$-C$_{20}$ alkynyl, (C$_0$-C$_6$ alkylene)-(C$_3$-C$_{12}$ cycloalkyl), or (C$_0$-C$_6$ alkylene)-(C$_3$-C$_{12}$ heterocycloalkyl), wherein said alkyl, alkenyl, alkynyl, alkylene, cycloalkyl and heteroalkyl are each optionally substituted with one or more (C$_0$-C$_6$ alkylene)-R$^7$;

or R$^5$ is (C$_0$-C$_6$ alkylene)-(C$_6$-C$_{14}$ aryl), or (C$_0$-C$_6$ alkylene)-(5-14 membered heteroaryl), wherein said aryl and heteroaryl are each optionally substituted with one or more R$_7$ and wherein said alkylene is optionally substituted with one or more (C$_0$-C$_6$ alkylene)-R$^8$.

In another aspect, R$^5$ and R$^6$ are attached to the adjacent carbon atoms of the thiazole ring and taken together to form a (4-8 membered) cycloalkyl, (4-8 membered) heterocycloalkyl, or C$_6$-C$_{10}$ aryl wherein said cycloalkyl and heteroalkyl are each substituted with one or more (C$_0$-C$_6$ alkylene)-R$^8$, (C$_0$-C$_6$ alkylene)-(C$_6$-C$_{14}$ aryl), and (C$_0$-C$_6$ alkylene)-(5-14 membered heteroaryl), and wherein said aryl and heteroaryl are each optionally substituted with one or more R$^7$.

In another aspect, R$^2$ is hydrogen and R$^3$ is methyl.

In another aspect, R$^6$ is H, —F, —CN, or —C$_1$-C$_4$ alkyl.

Specific embodiments of the present invention include the following compounds of Formula I, all pharmaceutically acceptable salts thereof, complexes thereof, and derivatives thereof that convert into a pharmaceutically active compound upon administration: 3-(2-{1-[(4-Chloro-benzenesulfonyl)-(2,5-difluoro-phenyl)-amino]-ethyl}-thiazol-5-yl)-propionic acidmethyl ester;

3-(2-{1-[(4-Chloro-benzenesulfonyl)-(2,5-difluoro-phenyl)-amino]-ethyl}-thiazol-5-yl)-propionic acid;

4-Chloro-N-(2,5-difluoro-phenyl)-N-{1-[5-(3-morpholin-4-yl-3-oxo-propyl)-thiazol-2-yl]-ethyl}-benzenesulfonamide;

4-Chloro-N-(2,5-difluoro-phenyl)-N-(1-{5-[3-(4-hydroxy-piperidin-1-yl)-3-oxo-propyl]-thiazol-2-yl}-ethyl)-benzenesulfonamide;

1-[3-(2-{1-[(4-Chloro-benzenesulfonyl)-(2,5-difluoro-phenyl)-amino]-ethyl}-thiazol-5-yl)-propionyl]-piperidine-3-carboxylic acid diethylamide;

4-Chloro-N-(2,5-difluoro-phenyl)-N-(1-{5-[3-oxo-3-(4-phenethyl-piperazin-1-yl)-propyl]-thiazol-2-yl}-ethyl)-benzenesulfonamide;

N-tert-Butyl-3-(2-{1-[(4-chloro-benzenesulfonyl)-(2,5-difluoro-phenyl)-amino]-ethyl}-thiazol-5-yl)-propionamide;

4-Chloro-N-(2,5-difluoro-phenyl)-N-{1-[5-(3-oxo-3-pyrrolidin-1-yl-propyl)-thaiazol-2-yl]-ethyl}-benzenesulfonamide;

4-Chloro-N-(2,5-difluoro-phenyl)-N-(1-{5-[3-(3-hydroxymethyl-piperidin-1-yl)-3-oxo-propyl]-thiazol-2-yl}-ethyl)-benzenesulfonamide;

3-(2-{1-[(4-Chloro-benzenesulfonyl)-(2,5-difluoro-phenyl)-amino]-ethyl}-thiazol-5-yl)-propionamide;

3-(2-{1-[(4-Chloro-benzenesulfonyl)-(2,5-difluoro-phenyl)-amino]-ethyl}-thiazol-5-yl)-N-(1-ethyl-propyl)-propionamide;

3-(2-{1-[(4-Chloro-benzenesulfonyl)-(2,5-difluoro-phenyl)-amino]-ethyl}-thiazol-5-yl)-N-(3,3-dimethyl-butyl)-propionamide;

4-Chloro-N-(2,5-difluoro-phenyl)-N-{1-[5-(3-hydroxy-3-methyl-butyl)-thiazol-2-yl]-ethyl}-benzene sulfonamide;

4-Chloro-N-(2,5-difluoro-phenyl)-N-{1-[5-(3-hydroxy-propyl)-thiazol-2-yl]-ethyl}-benzenesulfonamide;

4-Chloro-N-(2,5-difluoro-phenyl)-N-{1-[5-(3-oxo-propyl)-thiazol-2-yl]-ethyl}-benzenesulfonamide;

4-Chloro-N-(2,5-difluoro-phenyl)-N-{1-[5-(2-hydroxy-ethyl)-4-methyl-thiazol-2-yl]-ethyl}-benzene sulfonamide;

4-Chloro-N-(2,5-difluoro-phenyl)-N-{1-[5-(2-hydroxy-ethyl)-4-methyl-thiazol-2-yl]-propyl}-benzenesulfonamide;

4-Chloro-N-(2,5-difluoro-phenyl)-N-{1-[5-(2-hydroxy-ethyl)-4-methyl-thiazol-2-yl]-3-methyl-butyl}-benzenesulfonamide;

4-Chloro-N-(2,5-difluoro-phenyl)-N-[5-(2-hydroxy-ethyl)-4-methyl-thiazol-2-ylmethyl]-benzenesulfonamide;

4-Chloro-N-(2,5-difluoro-phenyl)-N-{[5-(2-hydroxy-ethyl)-4-methyl-thiazol-2-yl]-phenyl-methyl}-benzenesulfonamide;

N-(1-Benzothiazol-2-yl-ethyl)-4-chloro-N-(2,5-difluoro-phenyl)-benzenesulfonamide;

N-(1-Benzothiazol-2-yl-ethyl)-4-chloro-N-(2,5-difluoro-phenyl)-benzenesulfonamide;

4-Chloro-N-(2,5-difluoro-phenyl)-N-[1-(5-trifluoromethyl-benzothiazol-2-yl)-ethyl]-benzenesulfonamide;

4-Chloro-N-(2,5-difluoro-phenyl)-N-[1-(5-phenyl-thiazol-2-yl)-ethyl]-benzenesulfonamide;

4-Chloro-N-(2,5-difluoro-phenyl)-N-(1-thiazol-2-yl-ethyl)-benzenesulfonamide;

4-Chloro-N-(2,5-difluoro-phenyl)-N-[1-(4-methyl-5-vinyl-thiazol-2-yl)-ethyl]-benzenesulfonamide;

4-Chloro-N-(2,5-difluoro-phenyl)-N-[1-(5-formyl-4-methyl-thiazol-2-yl)-ethyl]-benzenesulfonamide;

4-Chloro-N-(2,5-difluoro-phenyl)-N-{1-[4-methyl-5-(4-methyl-piperazin-1-ylmethyl)-thiazol-2-yl]-ethyl}-benzenesulfonamide;

4-Chloro-N-(2,5-difluoro-phenyl)-N-{1-[5-(4-hydroxy-piperidin-1-ylmethyl)-4-methyl-thiazol-2-yl]-ethyl}-benzenesulfonamide;

2-(R)-[(2-{1-[(4-Chloro benzenesulfonyl)-(2,5-difluoro-phenyl)-amino]-ethyl}-4-methyl-thiazol-5-ylmethyl)-amino]-4-methyl-pentanoic acid amide;

4-Chloro-N-(2,5-difluoro-phenyl)-N-(1-{5-[(3-methoxy-propylamino)-methyl]-4-methyl-thiazol-2-yl}-ethyl)-benzenesulfonamide;

4-Chloro-N-(2,5-difluoro-phenyl)-N-[1-(4-methyl-5-piperidin-1-ylmethyl-thiazol-2-yl)-ethyl]-benzenesulfonamide;

4-Chloro-N-(2,5-difluoro-phenyl)-N-[1-(4-methyl-5-{[3-(2-oxo-pyrrolidin-1-yl)-propylamino]-methyl}-thiazol-2-yl)-ethyl]-benzenesulfonamide;

4-Chloro-N-(2,5-difluoro-phenyl)-N-(1-{4-methyl-5-[(2-pyridin-2-yl-ethylamino)-methyl]-thiazol-2-yl}-ethyl)-benzenesulfonamide;

4-Chloro-N-(2,5-difluoro-phenyl)-N-(1-{4-methyl-5-[(2-phenoxy-ethylamino)-methyl]-thiazol-2-yl}-ethyl)-benzenesulfonamide;

4-Chloro-N-(2,5-difluoro-phenyl)-N-(1-{5-[(5-hydroxy-1,5-dimethyl-hexylamino)-methyl]-4-methyl-thiazol-2-yl}-ethyl)-benzenesulfonamide;

N-{1-[5-(4-Acetyl-piperazin-1-ylmethyl)-4-methyl-thiazol-2-yl]-ethyl}-4-chloro-N-(2,5-difluoro-phenyl)-benzenesulfonamide;

1-(2-{1-[(4-Chloro-benzenesulfonyl)-(2,5-difluoro-phenyl)-amino]-ethyl}-4-methyl-thiazol-5-ylmethyl)-piperidine-4-carboxylic acid amide;

2-[(2-{1-[(4-Chloro-benzenesulfonyl)-(2,5-difluoro-phenyl)-amino]-ethyl}-4-methyl-thiazol-5-ylmethyl)-methyl-amino]-acetamide;

4-Chloro-N-(2,5-difluoro-phenyl)-N-{1-[4-methyl-5-(3-oxo-piperazin-1-ylmethyl)-thiazol-2-yl]-ethyl}-benzenesulfonamide;

4-Chloro-N-(2,5-difluoro-phenyl)-N-{1-[4-methyl-5-(5-oxo-[1,4]diazepan-1-ylmethyl)-thiazol-2-yl]-ethyl}-benzenesulfonamide;

3-[(2-{1-[(4-Chloro-benzenesulfonyl)-(2,5-difluoro-phenyl)-amino]-ethyl}-4-methyl-thiazol-5-ylmethyl)-amino]-propionamide;

2-[(2-{1-[(4-Chloro-benzenesulfonyl)-(2,5-difluoro-phenyl)-amino]-ethyl}-4-methyl-thiazol-5-ylmethyl)-amino]-acetamide;

2-[(2-{1-[(4-Chloro-benzenesulfonyl)-(2,5-difluoro-phenyl)-amino]-ethyl}-4-methyl-thiazol-5-ylmethyl)-amino]-N-methyl-acetamide;

4-Chloro-N-(2,5-difluoro-phenyl)-N-[1-(4-methyl-5-{[2-(2-oxo-pyrrolidin-1-yl)-ethylamino]-methyl}-thiazol-2-yl)-ethyl]-benzenesulfonamide;

4-Chloro-N-(2,5-difluoro-phenyl)-N-[1-(4-methyl-5-{[2-(5-methyl-4H-[1,2,4]triazol-3-yl)-ethylamino]-methyl}-thiazol-2-yl)-ethyl]-benzenesulfonamide;

4-Chloro-N-(2,5-difluoro-phenyl)-N-[1-(4-methyl-5-{[(4-methyl-thiazol-2-ylmethyl)-amino]-methyl}-thiazol-2-yl)-ethyl]-benzenesulfonamide;

4-Chloro-N-(2,5-difluoro-phenyl)-N-[1-(4-methyl-5-{[(pyrimidin-4-ylmethyl)-amino]-methyl}-thiazol-2-yl)-ethyl]-benzenesulfonamide;

4-Chloro-N-(2,5-difluoro-phenyl)-N-[1-(4-methyl-5-{[(5-methyl-4H-[1,2,4]triazol-3-ylmethyl)-amino]-methyl}-thiazol-2-yl)-ethyl]-benzenesulfonamide;

4-Chloro-N-(2,5-difluoro-phenyl)-N-(1-{5-[(2-methoxy-2-methyl-propylamino)-methyl]-4-methyl-thiazol-2-yl}-ethyl)-benzenesulfonamide;

3-(2-{1-[(4-Chloro-benzenesulfonyl)-(2,5-difluoro-phenyl)-amino]-ethyl}-4-methyl-thiazol-5-yl)-propionic acid methyl ester;

3-(2-{1-[(4-Chloro-benzenesulfonyl)-(2,5-difluoro-phenyl)-amino]-ethyl}-4-methyl-thiazol-5-yl)-propionic acid;

4-Chloro-N-(2,5-difluoro-phenyl)-N-(1-thiazol-5-yl-ethyl)-benzenesulfonamide;

4-Chloro-N-(2,5-difluoro-phenyl)-N-[1-(2-formyl-thiazol-5-yl)-ethyl]benzenesulfonamide;

5-{1-[(4-Chloro-benzenesulfonyl)-(2,5-difluoro-phenyl)-amino]-ethyl}-thiazole-2-carboxylic acid;

3-(5-{1-[(4-Chloro-benzenesulfonyl)-(2,5-difluoro-phenyl)-amino]-ethyl}-thiazol-2-yl)-propionic acid methyl ester;

3-(5-{1-[(4-Chloro-benzenesulfonyl)-(2,5-difluoro-phenyl)-amino]-ethyl}-thiazol-2-yl)-propionic acid;

5-{1-[(4-Chloro-benzenesulfonyl)-(2,5-difluoro-phenyl)-amino]-ethyl}-thiazole-2-carboxylic acid amide;
3-(5-{1-[(4-Chloro-benzenesulfonyl)-(2,5-difluoro-phenyl)-amino]-ethyl}-thiazol-2-yl)-propionamide;
3-(5-{1-[(4-Chloro-benzenesulfonyl)-(2,5-difluoro-phenyl)-amino]-ethyl}-thiazol-2-yl)-N-methyl-propionamide;
4-Chloro-N-(2,5-difluoro-phenyl)-N-{1-[2-(4-hydroxy-piperidin-1-ylmethyl)-thiazol-5-yl]-ethyl}-benzenesulfonamide;
1-(5-{1-[(4-Chloro-benzenesulfonyl)-(2,5-difluoro-phenyl)-amino]-ethyl}-thiazol-2-ylmethyl)-piperidine-3-carboxylic acid amide; and
4-Chloro-N-(2,5-difluoro-phenyl)-N-[1-(2-hydroxymethyl-thiazol-5-yl)-ethyl]-benzenesulfonamide;

and pharmaceutical accepted salts thereof.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by $(C_1-C_8)$alkyl;

(ii) where the compound of Formula I contains an alcohol functionality (—OH), an ether thereof, for example, a compound wherein the hydrogen of the alcohol functionality of the compound of Formula I is replaced by $(C_1-C_6)$alkanoyloxymethyl; and (iii) where the compound of Formula I contains a primary or secondary amino functionality (—NH$_2$ or —NHR where R≠H), an amide thereof, for example, a compound wherein, as the case may be, one or both hydrogens of the amino functionality of the compound of Formula I is/are replaced by $(C_1-C_{10})$alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—CH$_3$->—CH$_2$OH):

(ii) where the compound of Formula I contains an alkoxy group, an hydroxy derivative thereof (—OR->—OH);

(iii) where the compound of Formula I contains a tertiary amino group, a secondary amino derivative thereof (—NR$^1$R$^2$->—NHR$^1$ or —NHR$^2$);

(iv) where the compound of Formula I contains a secondary amino group, a primary derivative thereof (—NHR$^1$->—NH$_2$);

(v) where the compound of Formula I contains a phenyl moiety, a phenol derivative thereof (—Ph->—PhOH); and (vi) where the compound of Formula I contains an amide group, a carboxylic acid derivative thereof (—CONH$_2$->COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate.

Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of Formula II as hereinbefore defined, all salts, solvates and complexes thereof and all solvates and complexes of salts thereof as defined hereinbefore for compounds of Formula I. The invention includes all polymorphs of the aforementioned species and crystal habits thereof.

When preparing compounds of Formula I in accordance with the invention, it is open to a person skilled in the art to routinely select the form of compound of Formula II which provides the best combination of features for this purpose. Such features include, but are not limited to, the melting point, solubility, processability and yield of the intermediate form and the resulting ease with which the product may be purified on isolation.

Compounds of the Formula I of this invention, and their pharmaceutically acceptable salts, have useful pharmaceutical and medicinal properties. The compounds of Formula I, and their pharmaceutically acceptable salts inhibit the production of Aβ-peptide (thus, gamma-secretase activity) in mammals, including humans. Compounds of the Formula I, and their pharmaceutically acceptable salts, are therefore able to function as therapeutic agents in the treatment of the neurodegenerative and/or neurological disorders and diseases representatively enumerated below, for example Alzheimer's disease, in an afflicted mammal, including a human.

The present invention also relates to a pharmaceutical composition for treating a disease or condition in a mammal selected from the group consisting of Alzheimer's disease, hereditary cerebral hemorrhage with amyloidosis, cerebral amyloid angiopathy, a prion-mediated disease, inclusion body mypsitis, stroke, multiple sclerosis and Down's Syndrome including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or condition in a mammal selected from the group consisting of Alzheimer's disease and Down's Syndrome, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or a condition in a mammal selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, including a human, comprising an amount of a compound of the Formula I, or a pharmaceutically acceptable salt thereof, that is effective in treating such disease or condition, and a pharmaceutically acceptable carrier.

The present invention also relates to a pharmaceutical composition for treating a disease or a condition in a mammal selected from the group consisting of Alzheimer's disease and Down's Syndrome, including a human, comprising an amount of a compound of the Formula I, or a pharmaceutically acceptable salt thereof, that is effective in treating such disease or condition, and a pharmaceutically acceptable carrier.

The present invention also relates to a method of treating a disease or condition in a mammal selected from Alzheimer's disease, hereditary cerebral hemorrhage with amyloidosis, cerebral amyloid angiopathy, a prion-mediated disease, inclusion body myositis, stroke, multiple sclerosis and Down's Syndrome, including a human, comprising administering to said mammal an amount of a compound of the Formula I, or a pharmaceutically acceptable salt thereof, that is effective in inhibiting Aβ-production.

The present invention also relates to a method of treating a disease or condition in a mammal selected from Alzheimer's disease and Down's Syndrome, including a human, comprising administering to said mammal an amount of a compound of the Formula I, or a pharmaceutically acceptable salt thereof, that is effective in inhibiting Aβ-production.

The present invention also relates to a method of treating a disease or condition in a mammal selected from Alzheimer's disease, hereditary cerebral hemorrhage with amyloidosis, cerebral amyloid angiopathy, a prion-mediated disease, inclusion body myositis, stroke, multiple sclerosis and Down's Syndrome, including a human, comprising administering to said mammal an amount of a compound of the Formula I, or a pharmaceutically acceptable salt thereof, that is effective in treating such condition.

The present invention also relates to a method of treating a disease or condition in a mammal, selected from Alzheimer's disease and Down's Syndrome, including a human, comprising administering to said mammal an amount of a compound of the Formula I, or a pharmaceutically acceptable salt thereof, that is effective in treating such condition.

The compounds of Formula I may be used alone or used in combination with any other drug, including, but not limited to, any memory enhancement agent, e.g., Aricept™ and/or Namenda™, antidepressant agent, e.g., Zoloft™, anxiolytic, antipsychotic agent, e.g., Geodon™, sleep disorder agent, anti-inflammatory agent e.g., Celebrex™, Bextra™, etc., anti-oxidant agent, cholesterol modulating agent (for example, an agent that lowers LDL or increases HDL), e.g., Lipitor™ and anti-hypertension agent. Accordingly, the present invention also relates to the following pharmaceutical compositions and methods of treatment comprising a compound of the Formula I in combination with other drugs, such as those of the type described above.

The present invention also relates to a pharmaceutical composition for treating a disease or condition in a mammal associated with Aβ-peptide production, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™ and anti-hypertensive agent; and (c) a pharmaceutically acceptable carrier; wherein the active agents (a) and (b) are present in amounts that render the composition effective in treating such disease or condition.

The present invention also relates to a pharmaceutical composition for treating a disease or condition in a mammal selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™ and anti-hypertensive agent; and (c) a pharmaceutically acceptable carrier; wherein the active agents (a) and (b) are present in amounts that render the composition effective in treating such disease or condition.

The present invention also relates to a pharmaceutical composition for treating a disease or condition in a mammal selected from the group consisting of Alzheimer's disease and Down's Syndrome, in a mammal, including a human, comprising (a) a compound of the Formula I, or a pharmaceutically acceptable salt thereof; (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™ and anti-hypertensive agent; and (c) a pharmaceutically acceptable carrier; wherein the active agents (a) and (b) are present in amounts that render the composition effective in treating such disease or condition.

The present invention also relates to a method of treating a disease or condition in a mammal associated with Aβ-peptide production, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™ and anti-hypertensive agent; wherein the active agents (a) and (b) are present in amounts that render the composition effective in treating such disease or condition.

The present invention also relates to a method of treating a disease or condition in a mammal selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™ and anti-hypertensive agent; wherein the active agents (a) and (b) are present in amounts that render the composition effective in treating such disease or condition.

The present invention also relates to a method of treating a disease or condition in a mammal selected from the group consisting of Alzheimer's disease and Down's Syndrome, including a human, comprising administering to said mammal (a) a compound of the Formula I, or a pharmaceutically acceptable salt thereof; and (b) a memory enhancement agent, e.g., Aricept™ and/or Namenda™, antidepressant, e.g., Zoloft™, anxiolytic, antipsychotic agent, e.g., Geodon™, sleep disorder agent, anti-inflammatory agent, e.g., Celebrex™, Bextra™, etc., anti-oxidant agent, cholesterol modulating agent (for example, an agent that lowers LDL or increases HDL), e.g., Lipitor™ and anti-hypertensive agent; wherein the active agents (a) and (b) are present in amounts that render the composition effective in treating such disease or condition.

Compounds of the Formula I, or any of the combinations described in the immediately preceding paragraphs, may optionally be used in conjunction with a known P-glycoprotein inhibitor, such as verapamil.

References herein to diseases and conditions "associated with Aβ-peptide production" relate to diseases or conditions that are caused, at least in part, by Aβ-peptide and/or the production thereof. Thus, Aβ-peptide is a contributing factor, but not necessarily the only contributing factor, to "a disease or condition associated with Aβ-peptide production."

The compounds of Formula I, or their pharmaceutically acceptable salts may also be used to modulate or inhibit the Notch signaling pathway in organisms, including humans. The Notch signaling pathway is an evolutionarily conserved mechanism utilized by organisms, ranging from worms through humans, to regulate fate determination of various cell lineages. Notch belongs to the family of epidermal growth factor-like homeotic genes, which encode transmembrane proteins with variable numbers of epidermal growth factor-like repeats in the extracellular domain. There is increasing evidence for a role of the Notch pathway in human disease. All of the components of the pathway have yet to be identified, but among those identified to date, mutations that affect their interaction with each other can lead to a variety of syndromes and pathological conditions.

For example, Notch signaling is typically associated with cell fate decision. The finding that Notch activation stimulates capillary outgrowth suggests that Notch receptors must be activated to allow this process to occur. Therefore, Notch modulation provides a method for regulating angiogenesis. Specifically, modulation of Notch signaling can be used to modulate angiogenesis (e.g., by blocking Notch signaling to block angiogenesis). This inhibition of angiogenesis in vivo can be used as a therapeutic means to treat a variety of diseases, including but not limited to cancer, diabetic retinopathy, rheumatoid arthritis, psoriasis, inflammatory bowel disease and arteriosclerosis.

The Notch pathway is also implicated in the development and maturation of T cells, as described in Radtke, F. et al., *Immunity* 10:547-558, 1999. The compounds of Formula I, and their pharmaceutically acceptable salts are therefore useful candidates for modulating the immune system, including the treatment of inflammation, asthma, graft rejection, graft versus host disease, autoimmune disease and transplant rejection.

In addition, a number of studies published between 2002 and 2004 have provided convincing evidence that Notch signaling is frequently elevated in a variety of human tumors (including, but not limited to breast, prostate, pancreas and T-cell acute lymphoblastic leukemia). One key study provides a strong genetic link to Notch's role in important tumor types. Specifically, Weijzen et al. demonstrated that Notch signaling maintains the neoplastic phenotype in human Ras-transformed cells. Weijzen et al. (2002) *Nature Med* 8: 979. Because 30% of human malignancies may carry activating mutations in at least one of the three isoforms of Ras, this finding raises the possibility that Notch inhibitors would be a powerful addition to anti-cancer therapy. Another study's findings support a central role for aberrant Notch signaling in the pathogenesis of human T cell acute lymphoblastic leukemia/lymphoma. Pear et al., *Current Opinion in Hematology* (2004), 11(6), 426-433.

Accordingly, the compounds of Formula I, and their pharmaceutically acceptable salts, may be used for treating a disease or condition selected from the group consisting of cancer, arteriosclerosis, diabetic retinopathy, rheumatoid arthritis, psoriasis, inflammatory bowel disease inflammation, asthma, graft rejection, graft versus host disease, autoimmune disease and transplant rejection.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

Compounds of the Formula I, and their pharmaceutically acceptable salts, may be prepared as described in the following reaction Schemes and discussion. Unless otherwise indicated, as referred to in the reaction schemes and discussion that follow, $R^1$ to $R^{13}$, X, A and Z are as defined above.

The compounds of Formula I may have asymmetric carbon atoms and may therefore exist as racemic mixtures, diastereoisomers, or as individual optical isomers.

Separation of a mixture of isomers of compounds of Formula I into single isomers may be accomplished according to conventional methods known in the art.

The compounds of the Formula I may be prepared by the methods described below, together with synthetic methods known in the art of organic chemistry, or modifications and derivatisations that are familiar to those of ordinary skill in the art. Preferred methods include, but are not limited to, those described below.

The reactions described below are performed in solvents that are appropriate to the reagents and materials employed and that are suitable for use in the reactions described. In the description of the synthetic methods described below, it is also to be understood that all reaction conditions, whether actual or proposed, including choice of solvent, reaction temperature, reaction duration time, reaction pressure, and other reaction conditions (such as anhydrous conditions, under argon, under nitrogen, etc.), and work up procedures, are those conditions that are standard for that reaction, as would be readily recognized by one of skill in the art. Alternate methods may also be used.

Method I:

Scheme 1:

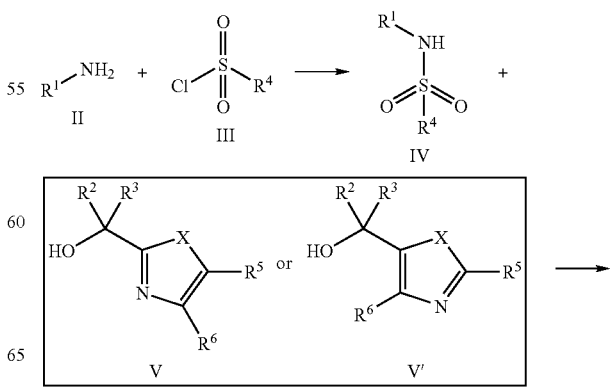

-continued

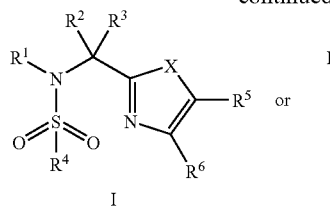

I

Compounds of Formula I (when $R^2$ or $R^3$ is hydrogen) can be prepared as illustrated in reaction scheme 1. Sulfonamide of formula IV can be prepared by treating commercially available or easily prepared amine II with a proper sulfonylating reagent, such as sulfonyl chloride III in an aprotic solvent such as methylene chloride in the presence of base. Such bases include triethylamine, pyridine and preferably with catalytic amount of 4-dimethylamino pyridine (DMAP). Sulfonamide IV is then subject to Mitsunobu condensation with compounds of formula V and V' to yield compound of formula I. A representative Mitsunobu condition includes the use of triphenylphosphine, DEAD or DIAD in proper solvents such as THF or toluene.

Scheme 2:

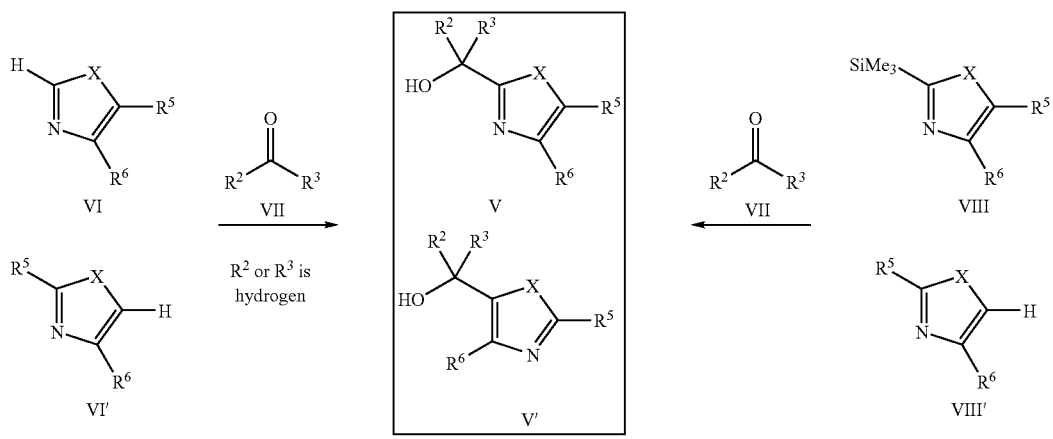

As shown in Scheme 2, when X is S, compounds of formula V and V' can be conveniently prepared by deprotonation of VI and VI' with strong bases, such as butyl lithium, sec-butyl lithium and tert-butyl lithium, at suitable temperature in proper solvents such as THF, followed by trapping the resultant anion with aldehyde VII (For a similar procedure in literature, see: Breslow; McNeils J. Am. Chem. Soc. 1959, 81, 3080; Berauld, J.; Metzger, J. Bull. Soc. Chim. Fr. 1962, 2072-2074; Noyce, D. S.; Fike, S. A. J. Org. Chem., 1973, 38, 3318.). Alternatively, the trapping can be carried out with trimethylsilyl substituted thiazole VIII and VIII' using a fluoride source, such as TBAF or cesium fluoride in an aprotic solvent such as THF or methylene chloride (for a similar procedure in literature, see: Tourwe, D.; Piron. J.; Defreyn, P.; Binst, G. V. Tetrahedron Lett. 1993,34. 5499).

Scheme 3:

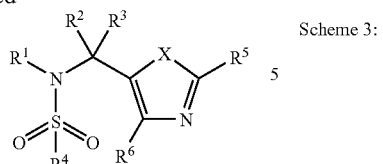

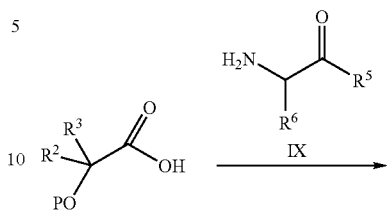

-continued

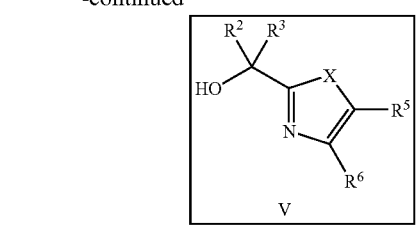

Alternatively, compounds of formula V can be synthesized as shown in Scheme 3. Commercially available or easily prepared alpha-hydroxyl carboxylic acid with suitable hydroxyl protecting groups (for examples, see: Protecting Groups in Organic Synthesis by Greene, T. W. and Wuts, P. G. W., 1999, 3rd edition, John Wiley & Sons, Inc.) was coupled with substituted alpha amino ketone or aldehyde IX via well-known amide coupling procedure in the art, such as carbodiimide, i.e. 1,3-dicyclohexylcarbodiimide (DCC), O-(1,2-dihydro-2-oxo-1-pyridyl)-N,N,N',N'-tetramethyluronium tetrafluoroborate (TPTU), 1,3-diisopropylcarbodiimide, 1-(3-dimethylaminopropyl)-3-ethylcarbodiimide (EDAC or EDCl), 2-(1H-benzotriazole-1-yl)-1,1,3,3-tetramethyluronium tetrafluoroborate (TBTU), PyBOP (benzotriazole-1-yl)-oxy-tris-pyrrolidino-phosphonium hexafluorophosphate), N-cyclohexylcarbodiimide, or N'-methylpolystyrene in the presence or absence of 1-hydroxy-benzotriazole (HOBt), in a suitable solvent such as dichloromethane (CH$_2$Cl$_2$), chloroform (CHCl$_3$), tetrahydrofuran (THF), diethyl ether (Et$_2$O), 1,4-dioxane, acetonitrile (CH$_3$CN), toluene, N,N-dimethylformamide (DMF).e. The resultant amide XI was then treated with Lawesson's reagent at elevated temperature in aprotic solvents such as toluene or benzene to form the heteroaryl ring wherein X is S. (Scheibye, S.; Kristensen, J.; Lawesson, S. O. *Tetrahedron*, 1979, 35, 1339) or with phosphorus oxytrichloride (POCl$_3$) at elevated temperature in an aprotic solvent such as toluene or benzene to form the heteroaryl ring wherein X is O. Subsequent removal of protecting group using well-established procedures in the art (see: Protecting Groups in Organic Synthesis by Greene, T. W. and Wuts, P. G. W., 1999, 3rd edition, John Wiley & Sons, Inc.) yields alpha-hydroxyl thiazole V.

Method II

Scheme 4:

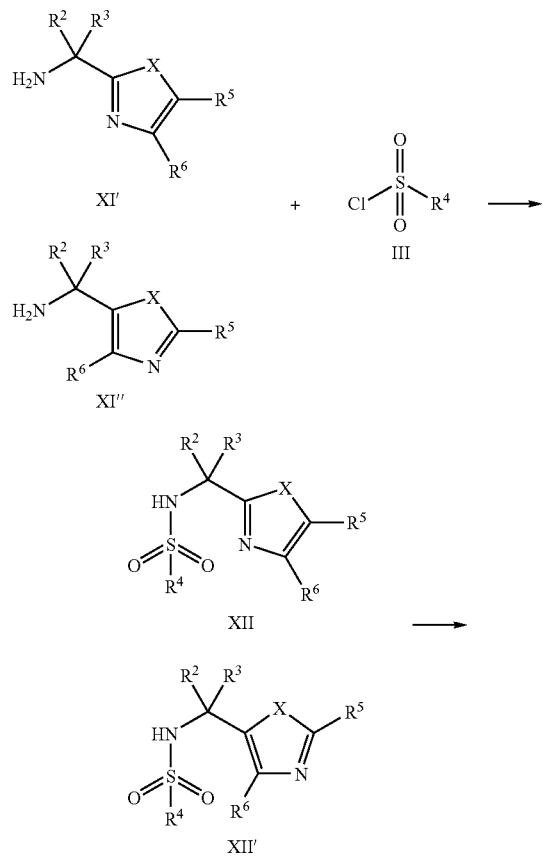

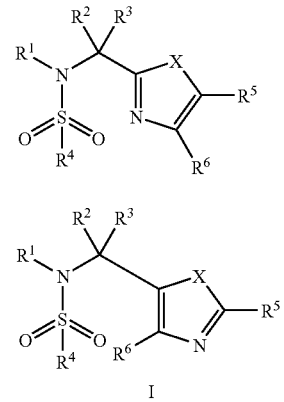

An alternative synthesis of compounds of formula I is shown in Scheme 4. Alpha-amino heteroaryl XI' and XI", either commercially available or derived from alpha-hydroxyl heteroaryl V and V' following well-established literature procedures (see Comprehensive Organic Transformations, A Guide to Functional Group Preparations, Larock, R. C., 1989, VCH Publishers Inc, ISBN 0-89573-710-8, pp 419-420): converting the hydroxyl group to a good leaving group such as mesylate, tosylate or triflate, then displaced with azide (N$_3^-$) following by reduction. XI' or XI" was condensed with a proper sulfonylating reagent, such as sulfonyl chloride III on an aprotic solvent such as methylene chloride in the presence of a suitable base. Such bases include triethylamine, pyridine and preferably with a catalytic amount of 4-dimethylamino pyridine (DMAP) to give sulfonamide XII and XII'. In one method for the conversion of sulfonamide XII and XII' to the compounds of formula I, XII or XII' was treated with a suitable base such as potassium carbonate, cesium carbonate or potassium t-butoxide and an alkylating agent such as alkyl bromide, alkyl iodide and alkyl mesylate in an aprotic solvent such as tetrahydrofuran (THF) or dimethyl formamide (DMF) with or without heating. An alternative method for the conversion of XII or XII' to compounds of formula I calls for a Mitsunobu condensation with R$^1$—OH. A representative Mitsunobu condition includes the use of triphenylphosphine, di-t-ethyl azadicarboxylate (DEAD), di-isopropyl azadicarboxylate (DIAD) or di-t-butyl azadicarboxylate in a proper solvent such as THF or toluene.

Method III

Scheme 5:

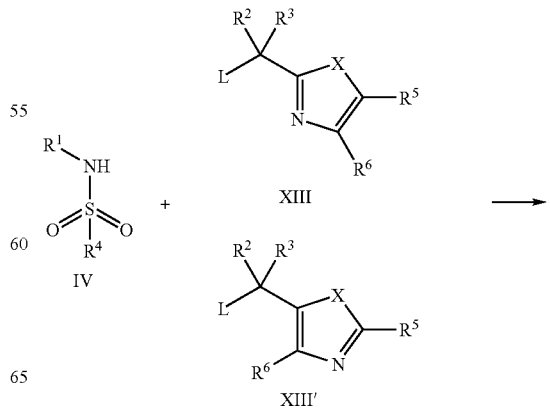

-continued

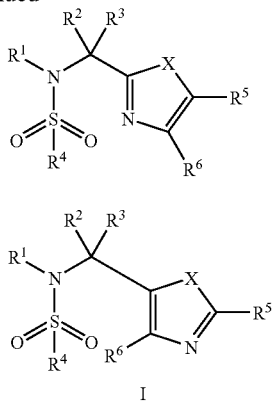

In addition, compound of formula I can be synthesized by treating sulfonamide IV with XIII and XIII', wherein L is a good leaving group such as I, Br, mesylate, tosylate or triflate, in the presence of a suitable base such as sodium hydride, potassium carbonate, cesium carbonate or potassium t-butoxide in an aprotic solvent such as tetrahydrofuran (THF) or dimethyl formamide (DMF) with or without heating. Compound of formula XIII and XIII' can be prepared from alpha-hydroxyl heteroaryls of formula V and V' following well-established procedures in the art (Comprehensive Organic Transformations, A Guide to Functional Group Preparations, Larock, R. C., 1989, VCH Publishers Inc, ISBN 0-89573-710-8).

The starting materials used in the procedures of the above Schemes, the syntheses of which are not described above, are either commercially available, known in the art or readily obtainable from known compounds using methods that will be apparent to those skilled in the art.

The compounds of Formula I, and the intermediates shown in the above reaction schemes, may be isolated and purified by conventional procedures, such as recrystallization or chromatographic separation, such as on silica gel, either with an ethyl acetate/hexane elution gradient, a methylene chloride/methanol elution gradient, or a chloroform/methanol elution gradient. Alternatively, a reverse phase preparative HPLC or chiral HPLC separation technique may be used.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

Pharmaceutically acceptable salts of the compounds of Formula I may be prepared in a conventional manner by treating a solution or suspension of the corresponding free base or acid with one chemical equivalent of a pharmaceutically acceptable acid or base. Conventional concentration or crystallization techniques may be employed to isolate the salts. Suitable acids, include, but are not limited to, acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic and related acids. Suitable bases include, but are not limited to, sodium, potassium and calcium.

A compound of the Formula I of the present invention, or pharmaceutically acceptable salt thereof, may be administered to mammals via either the oral, parenteral (such as subcutaneous, intravenous, intramuscular, intrasternal and infusion techniques), rectal, intranasal, topical or transdermal (e.g., through the use of a patch) routes. In general, these compounds are most desirably administered in doses ranging from about 0.1 mg to about 1000 mg per day, in single or divided doses (i.e., from 1 to 4 doses per day), although variations will necessarily occur depending upon the species, weight, age and condition of the subject being treated, as well as the particular route of administration chosen. However, a dosage level that is in the range of about 0.1 mg/kg to about 5 gm/kg body weight per day, preferably from about 0.1 mg/kg to about 100 mg/kg body weight per day, is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dosage levels are first divided into several small doses for administration throughout the day. Variations based on the aforementioned dosage range may be made by a physician of ordinary skill.

A compound of the Formula I of the present invention may be administered alone or in combination with pharmaceutically acceptable carriers or diluents by either of the routes previously indicated, and such administration may be carried out in single or multiple doses. Suitable pharmaceutical carriers include solid diluents or fillers, sterile aqueous media and various non-toxic organic solvents, etc. The pharmaceutical compositions formed by combining a compound of the Formula I, or a pharmaceutically acceptable salt thereof, with a pharmaceutically acceptable inert carrier, can then be readily administered in a variety of dosage forms such as tablets, capsules, lozenges, troches, hard candies, powders, sprays, creams, salves, suppositories, jellies, gels, pastes, lotions, ointments, aqueous suspensions, injectable solutions, elixirs, syrups, and the like. Moreover, oral pharmaceutical compositions may be suitably sweetened and/or flavored.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing a compound of the Formula I of the present invention or a pharmaceutically acceptable salt thereof in either sesame or peanut oil, in aqueous propylene glycol or in sterile aqueous solutions may be employed. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The compounds of Formula I of the present invention are useful in inhibiting Aβ-peptide production (thus, gamma-secretase activity) in mammals, and therefore they are able to function as therapeutic agents in the treatment of the aforementioned disorders and diseases in an afflicted mammal.

A specific compound of the Formula I can be determined to inhibit Aβ-peptide production using biological assays known to those of ordinary skill in the art, for example the assays described below.

The activity of compounds of the Formula I of the present invention in inhibiting gamma-secretase activity was determined in a solubilized membrane preparation generally according to the description provided in McLendon et al. *Cell-free assays for γ-secretase activity, The FASEB Journal* (Vol. 14, December 2000, pp. 2383-2386). Using such assay, compounds of the present invention were determined to have an $IC_{50}$ activity for inhibiting gamma-secretase activity of less than about 100 micromolar.

In the examples that follow, commercial reagents were used without further purification. Purification by chromatography was done on prepacked silica columns from Biotage (Dyax Corp, Biotage Division, Charlottesville, Va.). Proton nuclear magnetic resonance ($^1$H NMR) spectra were recorded in deuterated solvents on a Varian INOVA400 (400 MHz) spectrometer (Varian NMR Systems, Palo Alto, Calif.). Chemical shifts are reported in parts per million (ppm, δ) relative to $Me_4Si$ (δ 0.00). Proton NMR splitting patterns are designated as singlet (s), doublet (d), triplet (t), quartet (q), quintet (quin), sextet (sex), septet (sep), multiplet (m) apparent (ap) and broad (br). Coupling constants are reported in hertz (Hz). Mass spectra (MS) were obtained using a Waters ZMD mass spectrometer using flow injection atmospheric pressure chemical ionization (APCI) (Waters Corporation, Milford, Mass.). Gas chromatography with mass detection (GCMS) were obtained using a Hewlett Packard HP 6890 series GC system with a HP 5973 mass selective detector and a HP-1 (crosslinked methyl siloxane) column (Agilent Technologies, Wilmington, Del.). LC-MS spectra were recorded on a Water ZQ 1525μ Mass Spectrometry with Electrospray and a Binary HPLC Pump at 25° C. using gradient elution. Solvent A is 98% water, 2% acetonitrile with 0.01% formic acid, Solvent B is 100% acetonitrile with 0.005% formic acid. A linear gradient over 3.55 min was used starting at 95% A, 5% B and ending at 0% A, 100% B with a flow rate of 1 mL/min. Room temperature (RT) refers to 20-25° C. The abbreviations "h" and "hrs" refer to "hours".

The following examples illustrate the present invention. It is to be understood, however, that the invention, as fully described herein and as recited in the claims, is not intended to be limited by the details of the following examples.

EXAMPLES

Intermediate 1: 2-(4-Methoxy-benzyloxy)-propionic Acid Methyl Ester

To a stirred suspension of NaH (4.6 g, 60% in mineral oil, 115 mmol) in anhydrous DMF (500 mL) under $N_2$ at 0° C. was added methyl lactate (10 g, 96.1 mmol) dropwise. After the addition was complete, the reaction mixture was stirred for 1 h. PMBCl (15.6 mL, 115 mmol) was then added slowly, followed by the addition of TBAI (7.1 g, 19.2 mmol). The reaction mixture was then stirred at room temperature for 16 h. The mixture was then partitioned between EtOAc (1000 mL) and water (1000 mL). The aqueous layer was further extracted with EtOAc (500 mL). The organic layers were combined and washed with water (500 mL), brine (500 mL) and was dried with sodium sulfate. The solvent was removed in vacuo and the residue was purified with hexane/EtOAc (6:1) to give 12.3 g (57%) of yellowish oil as product. 1H-NMR ($CDCl_3$, 400 MHz) δ (ppM): 7.26 (d, 2H, J=8.7 Hz), 6.85 (d, 2H, J=8.7 Hz), 4.58 (d, 1H, J=11.2 Hz), 4.36 (d, 1H, J=11.2 Hz), 4.02 (quartet, 1H, J=6.7 Hz), 3.78 (s, 3H), 3.73 (s, 3H), 1.39 (d, 3H, J=6.7 Hz).

Intermediate 2: 2-(4-Methoxy-benzyloxy)-propionic Acid

To a stirred solution of 2-(4-methoxy-benzyloxy)-propionic acid methyl ester (12.3 g, 55 mmol) in THF (100 mL), MeOH (50 mL) and water (50 mL) at room temperature was added LiOH (6.6 g, 275 mmol). The reaction mixture was stirred for 38 h. The reaction mixture was adjusted to PH=1 with 1N HCl aqueous solution and extracted with EtOAc. The organic layer was dried with sodium sulfate. The mixture was filtered and the solvent was removed in vacuo to give 6.3 g (55%) of yellow oil as product. 1H-NMR ($CDCl_3$, 400 MHz) δ (ppM): 7.26 (d, 2H, J=8.7 Hz), 6.86 (d, 2H, J=8.7 Hz), 4.58 (d, 1H, J=11.2 Hz), 4.47 (d, 1H, J=11.2 Hz), 4.08 (quartet, 1H, J=7.1 Hz), 3.79 (s, 3H), 1.22 (d, 3H, J=7.1 Hz).

Intermediate 3: 5-[2-(4-Methoxy-benzyloxy)-propionylamino]-4-oxo-pentanoic Acid Methyl Ester To a stirred solution of 2-(4-methoxy-benzyloxy)-propionic acid (6.1 g, 29 mmol) in THF (100 mL) under N2 at 0° C. was added triethylamine (4.25 mL, 30.5 mmol), followed by the dropwise addition of isobutyl chloroformate (3.8 mL, 29 mmol). After the addition was complete, the resultant suspension was stirred at 0° C. for 30 min. Additional triethylamine (4.25 mL, 30.5 mmol) was added followed by the addition of 5-Amino-4-oxo-pentanoic acid methyl ester HCl salt (5.3 g, 29 mmol). The reaction mixture was then warmed to room temperature and stirred overnight. The reaction mixture was diluted with EtOAc (600 mL) and washed with water (500 mL), brine (500 mL) and was dried with sodium sulfate. The solvent was removed in vacuo and the residue was purified with hexane/EtOAc (1:1) to give 3.5 g (36%) of yellowish oil as product. LC-MS (ES+): 338 [M+], retention time 1.8 min; 1H-NMR ($CDCl_3$, 400 MHz) δ (ppM): 7.29 (d, 2H, J=8.3 Hz), 6.89 (d, 2H, J=8.3 Hz), 4.54 (d, 1H, J=11.2 Hz), 4.48 (d, 1H, J=11.2 Hz), 4.26 (dd, 1H, J=16.4, 5.4 Hz), 4.13 (dd, 1H, J=16.4, 5.4 Hz), 3.96 (quartet, 1H, J=6.6 Hz), 3.80 (s, 3H), 3.68 (s, 3H), 2.74 (m, 2H), 2.67 (m, 2H), 1.40 (d, 3H, J=6.6 Hz).

Intermediate 4: 3-{2-[1-(4-Methoxy-benzyloxy)-ethyl]-thiazol-5-yl}-propionic Acid Methyl Ester To a stirred solution of 5-[2-(4-methoxy-benzyloxy)-propionylamino]-4-oxo-pentanoic acid methyl ester (3.5 g, 10.4 mmol) in toluene (35 mL) under $N_2$ at room temperature was added lawesson's reagent (4.2 g, 10.4 mmol) in one portion. The reaction mixture was then heated to reflux for 1 h. The reaction mixture was cooled to room temperature and diluted with EtOAc. The mixture was washed with water (500 mL), brine (500 mL) and dried with sodium sulfate. The solvent was removed in vacuo and the residue was purified with hexane/EtOAc (5:1) to give 1.1 g (32%) of colorless oil as product. MS (APCI, ES+): 336; 1H-NMR (CDCl$_3$, 400 MHz) δ (ppM): 7.39 (s, 1H), 7.23 (d, 2H, J=2.0 Hz), 6.86 (d, 2H, J=2.1 Hz), 4.74 (quartet, 1H, J=6.6 Hz), 4.50 (d, 1H, J=11.2 Hz), 4.42 (d, 1H, J=11.2 Hz), 3.78 (s, 3H), 3.68 (s, 3H), 3.13 (t, 2H, J=7.5 Hz), 2.67 (t, 2H, J=7.5 Hz), 1.54 (d, 3H, J=6.6 Hz).

Intermediate 5:
3-[2-(1-Hydroxy-ethyl)-thiazol-5-yl]-propionic Acid Methyl Ester To a stirred solution of 3-{2-[1-(4-methoxy-benzyloxy)-ethyl]-thiazol-5-yl}-propionic acid methyl ester (1.0 g, 3.0 mmol) in 20:1 CH$_2$Cl$_2$:H$_2$O (21 mL) under N$_2$ at room temperature was added DDQ (680 mg, 3.0 mmol) in one portion. The reaction mixture was stirred for 5 h. Small amount of starting material still present. Additional DDQ (200 mg, 0.88 mmol) was added and the reaction mixture was stirred for additional 2 h. The reaction mixture was then diluted with CH$_2$Cl$_2$ and washed with saturated NaHCO$_3$ aqueous solution. The aqueous layer was further extracted with CH$_2$Cl$_2$. The organic layers were combined and washed with water (500 mL), brine (500 mL) and dried with sodium sulfate. The solvent was removed in vacuo and the residue was purified with hexane/EtOAc (1:1) to give 330 mg (51%) of brownish oil as product. 1H-NMR (CDCl$_3$, 400 MHz) δ (ppM): 7.39 (s, 1H), 5.04 (quartet, 1H, J=6.6 Hz), 3.67 (s, 3H), 3.11 (t, 2H, J=6.6 Hz), 2.76 (s, br, 1H), 2.65 (t, 2H, J=7.0 Hz), 1.58 (d, 3H, J=6.6 Hz).

Intermediate 6: 4-Chloro-N-(2,5-difluoro-phenyl)-benzenesulfonamide

To a stirred solution of 2,5-difluoroaniline (0.95 mL, 9.5 mmol) in pyridine (50 mL) under N$_2$ at room temperature was added 4-chlorobenzene sulfonyl chloride (2.0 g, 9.5 mmol) in one portion. The reaction mixture was stirred for 22 h. The reaction mixture was concentrated in vacuo and the residue was dissolved in CH$_2$Cl$_2$ (80 mL). The solution was washed with brine (500 mL) and dried with sodium sulfate. The solvent was removed in vacuo and the residue was purified with hexane/EtOAc (6:1) to give 2.4 g (83%) of white solid as product. 1H-NMR (CDCl$_3$, 400 MHz) δ (ppM): 7.72 (d, 2H, J=7.7 Hz), 7.42 (d, 2H, J=7.7 Hz), 7.33 (m, 1H), 6.92 (m, 1H), 6.71-6.77 (m, 2H).

Example 1

3-(2-{1-[(4-Chloro-benzenesulfonyl)-(2,5-difluoro-phenyl)-amino]-ethyl}-thiazol-5-yl)-propionic Acid-methyl Ester To a stirred solution of triphenylphosphine (330 mg, 1.26 mmol) in toluene (5 mL) under N$_2$ at room temperature was added intermediate 4-chloro-N-(2,5-difluoro-phenyl) benzenesulfonamide (304 mg, 1.0 mmol), followed by slow addition of DEAD (198 uL, 1.26 mmol). After the addition was complete, a solution of 3-[2-(1-hydroxy-ethyl)-thiazol-5-yl]-propionic acid methyl ester (180 mg, 0.84 mmol) in toluene (5 mL) was added dropwise. The reaction mixture was stirred for 16 h and was then diluted with EtOAc. The solution was washed with water, brine and dried with sodium sulfate. The solvent was removed in vacuo and the residue was purified with hexane/EtOAc (3:1) to give 235 mg (56%) of a colorless oil as product. MS (APCI) ES+: 501, ES−: 499. 1H-NMR (CD$_3$OD, 400 MHz) δ (ppM): 7.76 (d, 2H, J=8.3 Hz), 7.58 (d, 2H, J=8.3 Hz), 7.34 (s, 1H), 7.18 (m, 3H), 5.83 (quartet, 1H, J=7.0 Hz), 3.66 (s, 3H), 3.11 (t, 2H, J=7.5 Hz), 2.65 (t, 2H, J=7.5 Hz), 1.52 (d, 3H, J=6.6 Hz).

Example 2

3-(2-{1-[(4-Chloro-benzenesulfonyl)-(2,5-difluoro-phenyl)-amino]-ethyl}-thiazol-5-yl)-propionic Acid To a stirred solution of 3-(2-{1-[(4-chloro-benzenesulfonyl)-(2,5-difluoro-phenyl)-amino]-ethyl}-thiazol-5-yl)-propionic acidmethyl ester (20 mg, 0.04 mmol) in THF (1 mL) and water (1 mL) at room temperature was added LiOH (4.8 mg, 0.2 mmol). The reaction mixture was stirred for 4 h. No starting material was left. The reaction mixture was adjusted to PH=1 with 1N HCl aqueous solution and extracted with EtOAc. The organic layer was then dried with sodium sulfate and the solvent was removed in vacuo to give 15 mg (77%) of colorless oil as product. LC-MS (ES+): 487 [M+l], retention time 2.5. 1H-NMR (CD$_3$OD, 400 MHz)δ (ppM): 7.74 (d, 2H, J=8.7 Hz), 7.58 (d, 2H, J=8.8 Hz), 7.36 (s, 1H), 7.18 (m, 3H), 5.83 (quartet, 1H, J=7.0 Hz), 3.10 (t, 2H, J=7.5 Hz), 2.61 (t, 2H, J=7.5 Hz), 1.52 (d, 3H, J=7.0 Hz).

Example 3

4-Chloro-N-(2,5-difluoro-phenyl)-N-{1-[5-(3-morpholin-4-yl-3-oxo-propyl)-thiazol-2-yl]-ethyl}-benzenesulfonamide To a stirred solution of 3-(2-{1-[(4-chloro-benzenesulfonyl)-(2,5-difluoro-phenyl)-amino]-ethyl}-thiazol-5-yl)-propionic acid (15 mg, 0.03 mmol) in DMF (1 mL) under N$_2$ at room temperature was added iPr$_2$NEt (10 uL, 0.07 mmol), EDCI (7.0 mg, 0.037 mmol) and HOBt (5.0 mg, 0.037 mmol). The mixture was stirred to form a homogeneous solution and morpholine (3.2 mg, 0.037 mmol) was added. The reaction mixture was stirred at room temperature for 16 h and was then diluted with EtOAc. The solution was washed with water, brine and dried with sodium sulfate. The solvent was removed in vacuo and the residue was purified with hexane/EtOAc (1:3) to give 2.4 mg of product. LC-MS (ES+): 556 [M+l], retention time 2.5 min. 1H-NMR (CD$_3$OD, 400 MHz)δ (ppM): 7.74 (d, 2H, J=8.7 Hz), 7.58 (d, 2H, J=8.8 Hz), 7.36 (s, 1H), 7.18 (m, 3H), 5.80 (quartet, 1H, J=7.0 Hz), 3.60 (m, 4H), 3.54 (m, 2H), 3.48 (m, 2H), 3.09 (t, 2H, J=7.5 Hz), 2.67 (t, 2H, J=7.5 Hz), 1.50 (d, 3H, J=7.0 Hz).

The following examples were prepared using procedures similar to that of example 3:

| Example | MS | Name |
| --- | --- | --- |
| 4 | LC-MS (ES+): 2.3 min, 570 [M + 1] | 4-Chloro-N-(2,5-difluoro-phenyl)-N-(1-{5-[3-(4-hydroxy-piperidin-1-yl)-3-oxo-propyl]-thiazol-2-yl}-ethyl)-benzenesulfonamide |
| 5 | LC-MS (ES+): 2.6 min, 653 [M + 1] | 1-[3-(2-{1-[(4-Chloro-benzene-sulfonyl)-(2,5-difluoro-phenyl)-amino]-ethyl}-thiazol-5-yl)-propionyl]-piperidine-3-carboxylic acid diethylamide |
| 6 | LC-MS (ES+): 2.2 min, 659 [M + 1] | 4-Chloro-N-(2,5-difluoro-phenyl)-N-(1-{5-[3-oxo-3-(4-phenethyl-piperazin-1-yl)-propyl]-thiazol-2-yl}-ethyl)-benzenesulfonamide |

-continued

| Example | MS | Name |
|---|---|---|
| 7 | LC-MS (ES+): 2.8 min, 542 [M + 1] | N-tert-Butyl-3-(2-{1-[(4-chloro-benzenesulfonyl)-(2,5-difluoro-phenyl)-amino]-ethyl}-thiazol-5-yl)-propionamide |
| 8 | LC-MS (ES+): 2.5 min, 540 [M + 1] | 4-Chloro-N-(2,5-difluoro-phenyl)-N-{1-[5-(3-oxo-3-pyrrolidin-1-yl-propyl)-thiazol-2-yl]-ethyl}-benzenesulfonamide |
| 9 | LC-MS (ES+): 2.5 min, 584 [M + 1] | 4-Chloro-N-(2,5-difluoro-phenyl)-N-(1-{5-[3-(3-hydroxymethyl-piperidin-1-yl)-3-oxo-propyl]-thiazol-2-yl}-ethyl)-benzenesulfonamide |
| 10 | LC-MS (ES+): 2.3 min, 486 [M + 1] | 3-(2-{1-[(4-Chloro-benzene-sulfonyl)-(2,5-difluoro-phenyl)-amino]-ethyl}-thiazol-5-yl)-propionamide |
| 11 | LC-MS (ES+): 2.8 min, 556 [M + 1] | 3-(2-{1-[(4-Chloro-benzene-sulfonyl)-(2,5-difluoro-phenyl)-amino]-ethyl}-thiazol-5-yl)-N-(1-ethyl-propyl)-propionamide |
| 12 | LC-MS (ES+): 3.6 min, 567 [M + 1] | 3-(2-{1-[(4-Chloro-benzene-sulfonyl)-(2,5-difluoro-phenyl)-amino]-ethyl}-thiazol-5-yl)-N-(3,3-dimethyl-butyl)-propionamide |

Example 13

4-Chloro-N-(2,5-difluoro-phenyl)-N-{1-[5-(3-hydroxy-3-methyl-butyl)-thiazol-2-yl]-ethyl}-benzenesulfonamide To a stirred solution of 3-(2-{1-[(4-chloro-benzenesulfonyl)-(2,5-difluoro-phenyl)-amino]-ethyl}-thiazol-5-yl)-propionic acid methyl ester (48 mg, 0.96 mmol) in THF (4 mL) under $N_2$ at −78° C. was added MeMgBr (3M in $Et_2O$, 160 uL, 0.48 mmol). The mixture was slowly warmed to room temperature and stirred overnight. The reaction was quenched with 1 mL saturated $NH_4Cl$ aqueous solution and diluted with EtOAc. The solution was washed with water, brine and dried with sodium sulfate. The solvent was removed in vacuo and the residue was purified with 15-60% EtOAc in hexane to give 1.8 mg product and 30 mg recovered starting material. LC-MS (ES+): 501, retention time 3.5.

Example 14

4-Chloro-N-(2,5-difluoro-phenyl)-N-{1-[5-(3-hydroxy-propyl)-thiazol-2-yl]-ethyl}-benzenesulfonamide; and Example 15

4-Chloro-N-(2,5-difluoro-phenyl)-N-{1-[5-(3-oxo-propyl)-thiazol-2-yl]-ethyl}-benzenesulfonamide To a stirred solution of 3-(2-{1-[(4-Chloro-benzenesulfonyl)-(2,5-difluoro-phenyl)-amino]-ethyl}-thiazol-5-yl)-propionic acid (150 mg, 0.31 mmol) in THF (4 mL) under $N_2$ at −78° C. was added DIBAL (1M in THF, 0.93 mL, 0.93 mmol). The mixture was slowly warmed to room temperature and stirred overnight. Saturated Rochelle salt aqueous solution was added and the mixture was stirred for 1 h. The mixture was then diluted with $Et_2O$ and washed with water, brine and dried with sodium sulfate. The solvent was removed in vacuo and the residue was purified with hexane: EtOAc (1:1) in hexane to give 22 mg of 4-Chloro-N-(2,5-difluoro-phenyl)-N-{1-[5-(3-oxo-propyl)-thiazol-2-yl]-ethyl}-benzenesulfonamide, APCI (ES+): 471 [M+1]; LC-MS (ES+): 471 [M+1], 3.5 min; 26 mg of 4-Chloro-N-(2,5-difluoro-phenyl)-N-{1-[5-(3-hydroxy-propyl)-thiazol-2-yl]-ethyl}-benzenesulfonamide, LC-MS (ES+): 473 [M+1], 3.4 min.

Intermediate 7: 5-[2-(tert-Butyl-dimethyl-silanyl)-ethyl]-4-methyl-thiazole

To a stirred solution of 2-(4-methyl-thiazol-5-yl)-ethanol (10 g, 70.0 mmol) in THF (140 mL) under $N_2$ at room temperature was added imidazole (19 g, 280 mmol) and TBSCI (15.8 g, 105 mmol). The reaction mixture was stirred for 1 h. The reaction mixture was diluted in $Et_2O$ (500 mL) and was washed with 1N HCl, $NaHCO_3$ aq, brine and dried with sodium sulfate. The solvent was removed in vacuo to give 22 g clear liquid as product. 1H-NMR ($CDCl_3$, 400 MHz) δ (ppM): 8.53 (s, 1H), 3.75 (t, 2H, J=6.6 Hz), 2.93 (t, 2H, J=6.6 Hz), 2.37 (s, 3H), 0.85 (s, 9H), 0.07 (s, 6H).

Intermediate 8: 1-{5-[2-(tert-Butyl-dimethyl-silanyloxy)-ethyl]-4-methyl-thiazol-2-yl}-ethanol To a stirred solution of 5-[2-(tert-butyl-dimethyl-silanyl)-ethyl]-4-methyl-thiazole (17 g, 66.5 mmol) in THF (220 mL) under $N_2$ at −78° C. was added BuLi (2.5M in hexane, 32 mL, 80 mmol) dropwise over 45 min. Acetaldehyde (3.5 g, 80 mmol) was then added dropwise. The reaction mixture was then warmed to room temperature and stirred for 4.5 h. The reaction was quenched with $NH_4Cl$ aq and was then extracted with $Et_2O$ (3×200 mL). The combined ether layer was washed with water, brine and dried with sodium sulfate. The solvent was removed in vacuo and the residue was purified with hexane: EtOAc (1:1) to give 8.0 g clear oil as product. LC-MS (ES−): 302, retention time 3.5 min.

Example 16

4-Chloro-N-(2,5-difluoro-phenyl)-N-{1-[5-(2-hydroxy-ethyl)-4-methyl-thiazol-2-yl]-ethyl}-benzenesulfonamide To a stirred solution of triphenylphosphine (4.1 g, 15.8 mmol) in toluene (45 mL) under $N_2$ at room temperature was added 4-chloro-N-(2,5-difluoro-phenyl)-benzenesulfonamide (4.0 g, 13.2 mmol), followed by slow addition of DEAD (2.5 mL, 15.8 mmol). After the addition was complete, 1-{5-[2-(tert-butyl-dimethyl-silanyloxy)-ethyl]-4-methyl-thiazol-2-yl}-ethanol (4.0 g, 13.2 mmol) was added dropwise. The reaction mixture was stirred for 16 h and was then diluted with EtOAc. The solution was washed with water, brine and dried with sodium sulfate. The solvent was removed in vacuo and the residue was then dissolved in THF (100 mL) and TBAF (1M in THF, 14 mL) was added dropwise. The mixture was stirred at room temperature for 1 h and was then diluted with $Et_2O$ (500 mL) and washed with water, brine and dried with sodium sulfate. The solvent was removed in vacuo and the residue was purified using hexane:EtOAc (1:1) to give 0.7 g white solid as product. LC-MS (ES+): 473 [M+1], retention time 3.4 min.

The following examples were prepared via similar procedure using the corresponding thiazoles and aldehydes:

| Example | MS | Name |
|---|---|---|
| 17 | LC-MS (ES+): 3.4 min, 487 [M + 1] | 4-Chloro-N-(2,5-difluoro-phenyl)-N-{1-[5-(2-hydroxy-ethyl)-4-methyl-thiazol-2-yl]-propyl}-benzenesulfonamide |
| 18 | LC-MS (ES+): 3.6 min, 515 [M + 1] | 4-Chloro-N-(2,5-difluoro-phenyl)-N-{1-[5-(2-hydroxy-ethyl)-4-methyl-thiazol-2-yl]-3-methyl-butyl}-benzenesulfonamide |
| 19 | LC-MS (ES+): 2.5 min, 459 [M + 1] | 4-Chloro-N-(2,5-difluoro-phenyl)-N-[5-(2-hydroxy-ethyl)-4-methyl-thiazol-2-ylmethyl]-benzenesulfonamide |
| 20 | LC-MS (ES+): 2.8 min, 535 [M + 1] | 4-Chloro-N-(2,5-difluoro-phenyl)-N-{[5-(2-hydroxy-ethyl)-4-methyl-thiazol-2-yl]-phenyl-methyl}-benzenesulfonamide |
| 21 | LC-MS (ES+): 3.7 min, 465 [M + 1] | N-(1-Benzothiazol-2-yl-ethyl)-4-chloro-N-(2,5-difluoro-phenyl)-benzenesulfonamide |
| 22 | LC-MS (ES+): 3.8 min, 507 [M + 1] | N-(1-Benzothiazol-2-yl-ethyl)-4-chloro-N-(2,5-difluoro-phenyl)-benzenesulfonamide |
| 23 | LC-MS (ES+): 3.2 min, 533 [M + 1] | 4-Chloro-N-(2,5-difluoro-phenyl)-N-[1-(5-trifluoromethyl-benzothiazol-2-yl)-ethyl]-benzenesulfonamide |
| 24 | LC-MS (ES+): 3.3 min, 505 [M + 1] | 4-Chloro-N-(2,5-difluoro-phenyl)-N-[1-(5-phenyl-thiazol-2-yl)-ethyl]-benzenesulfonamide |
| 25 | LC-MS (ES+): 2.7 min, 415 [M + 1] | 4-Chloro-N-(2,5-difluoro-phenyl)-N-(1-thiazol-2-yl-ethyl)-benzenesulfonamide |
| 26 | LC-MS (ES+): 3.1 min, 455 [M + 1] | 4-Chloro-N-(2,5-difluoro-phenyl)-N-[1-(4-methyl-5-vinyl-thiazol-2-yl)-ethyl]-benzenesulfonamide |

Example 27

4-Chloro-N-(2,5-difluoro-phenyl)-N-[1-(5-formyl-4-methyl-thiazol-2-yl)-ethyl]-benzenesulfonamide To a stirred solution of 4-chloro-N-(2,5-difluoro-phenyl)-N-[1-(4-methyl-5-vinyl-thiazol-2-ethyl]-benzenesulfonamide (5.0 g, 11 mmol) in dioxane/H$_2$O (3:1, 44 mL) under N$_2$ at room temperature was added OsO$_4$ (2.7 mg, 0.001 mmol) and stirred for 5 min and NaIO$_4$ (4.6 g, 21.8 mmol) was then added in small portions. The reaction mixture was stirred at room temperature for 16 h and was then diluted with EtOAc. The solution was washed with water, brine and dried with sodium sulfate. The solvent was removed in vacuo and the residue was purified using hexane:EtOAc (3:1) to give 1.7 g white solid as product. LC-MS (ES$^+$): 457 [M+1], retention time 2.9 min.

Example 28

4-Chloro-N-(2,5-difluoro-phenyl)-N-{1-[4-methyl-5-(4-methyl-piperazin-1-ylmethyl)-thiazol-2-yl]-ethyl}-benzenesulfonamide To a stirred solution of 4-chloro-N-(2,5-difluoro-phenyl)-N-[1-(5-formyl-4-methyl-2-yl)-ethyl]-benzenesulfonamide (50 mg, 0.11 mmol) in MeOH (0.3 mL) and CH$_2$Cl$_2$ (0.3 mL) was added N-methyl piperazine (11 mg, 0.11 mmol), NaCNBH$_3$ (8.3 mg, 0.13 mmol) and ZnCl$_2$ (1.5 mg, 0.01 mmol) under N$_2$ at room temperature. The reaction mixture was stirred at room temperature for 16 h and was then diluted with EtOAc. The solution was washed with water, brine and dried with sodium sulfate. The solvent was removed in vacuo amd the residue was purified using 0-7% MeOH in CH$_2$Cl$_2$ to give 10 mg oil as product. LC-MS (ES$^+$): 541[M+1], retention time 1.8 min.

The following examples were prepared via similar procedures using the corresponding amines:

| Example | MS | Name |
|---|---|---|
| 29 | LC-MS (ES+): 1.8 min, 542 [M + 1] | 4-Chloro-N-(2,5-difluoro-phenyl)-N-{1-[5-(4-hydroxy-piperidin-1-ylmethyl)-4-methyl-thiazol-2-yl]-ethyl}-benzenesulfonamide |
| 30 | LC-MS (ES+): 2.1 min, 571 [M + 1] | 2-(R)-[(2-{1-[(4-Chloro benzene-sulfonyl)-(2,5-difluoro-phenyl)-amino]-ethyl}-4-methyl-thiazol-5-ylmethyl)-amino]-4-methyl-pentanoic acid amide |
| 31 | LC-MS (ES+): 2.0 min, 530 [M + 1] | 4-Chloro-N-(2,5-difluoro-phenyl)-N-(1-{5-[(3-methoxy propylamino)-methyl]-4-methyl-thiazol-2-yl}-ethyl)-benzene-sulfonamide |
| 32 | LC-MS (ES+): 1.9 min, 526 [M + 1] | 4-Chloro-N-(2,5-difluoro-phenyl)-N-[1-(4-methyl-5-piperidin-1-ylmethyl-thiazol-2-yl)-ethyl]-benzenesulfonamide |
| 33 | LC-MS (ES+): 2.1 min, 583 [M + 1] | 4-Chloro-N-(2,5-difluoro-phenyl)-N-[1-(4-methyl-5-{[3-(2-oxo-pyrrolidin-1-yl)-propylamino]-methyl}-thiazol-2-yl)-ethyl]-benzenesulfonamide |
| 34 | LC-MS (ES+): 2.3 min, 563 [M + 1] | 4-Chloro-N-(2,5-difluoro-phenyl)-N-(1-{4-methyl-5-[(2-pyridin-2-yl-ethyl-amino)-methyl]-thiazol-2-yl}-ethyl)-benzenesulfonamide |
| 35 | LC-MS (ES+): 2.3 min, 578 [M + 1] | 4-Chloro-N-(2,5-difluoro-phenyl)-N-(1-{4-methyl-5-[(2-phenoxy-ethylamino)-methyl]-thiazol-2-yl}-ethyl)-benzenesulfonamide |
| 36 | LC-MS (ES+): 2.0 min, 586 [M + 1] | 4-Chloro-N-(2,5-difluoro-phenyl)-N-(1-{5-[(5-hydroxy-1,5-dimethyl-hexyl-amino)-methyl]-4-methyl-thiazol-2-yl}-ethyl)-benzenesulfonamide |
| 37 | LC-MS (ES+): 2.0 min, 569 [M + 1] | N-{1-[5-(4-Acetyl-piperazin-1-ylmethyl)-4-methyl-thiazol-2-yl]-ethyl}-4-chloro-N-(2,5-difluoro-phenyl)-benzenesulfonamide |
| 38 | LC-MS (ES+): 1.9 min, 569 [M + 1] | 1-(2-{1-[(4-Chloro-benzenesulfonyl)-(2,5-difluoro-phenyl)-amino]-ethyl}-4-methyl-thiazol-5-ylmethyl)-piperidine-4-carboxylic acid amide |
| 39 | LC-MS (ES+): 1.9 min, 529 [M + 1] | 2-[(2-{1-[(4-Chloro-benzenesulfonyl)-(2,5-difluoro-phenyl)-amino]-ethyl}-4-methyl-thiazol-5-ylmethyl)-methyl-amino]-acetamide |
| 40 | LC-MS (ES+): 2.3 min, 541 [M + 1] | 4-Chloro-N-(2,5-difluoro-phenyl)-N-{1-[4-methyl-5-(3-oxo-piperazin-1-ylmethyl)-thiazol-2-yl]-ethyl}-benzenesulfonamide |
| 41 | LC-MS (ES+): 2.0 min, 555 [M + 1] | 4-Chloro-N-(2,5-difluoro-phenyl)-N-{1-[4-methyl-5-(5-oxo-[1,4]diazepan-1-ylmethyl)-thiazol-2-yl]-ethyl}-benzenesulfonamide |
| 42 | LC-MS (ES+): 1.8 min, 529 [M + 1] | 3-[(2-{1-[(4-Chloro-benzenesulfonyl)-(2,5-difluoro-phenyl)-amino]-ethyl}-4-methyl-thiazol-5-ylmethyl)-amino]-propionamide |
| 43 | LC-MS (ES+): 1.9 min, 515 [M + 1] | 2-[(2-{1-[(4-Chloro-benzenesulfonyl)-(2,5-difluoro-phenyl)-amino]-ethyl}-4-methyl-thiazol-5-ylmethyl)-amino]-acetamide |
| 44 | LC-MS (ES+): 1.9 min, 529 [M + 1] | 2-[(2-{1-[(4-Chloro-benzenesulfonyl)-(2,5-difluoro-phenyl)-amino]-ethyl}-4-methyl-thiazol-5-ylmethyl)-amino]-N-methyl-acetamide |
| 45 | LC-MS (ES+): 2.0 min, 569 [M + 1] | 4-Chloro-N-(2,5-difluoro-phenyl)-N-[1-(4-methyl-5-{[2-(2-oxo-pyrrolidin-1-yl)-ethylamino]-methyl}-thiazol-2-yl)-ethyl]-benzenesulfonamide |
| 46 | LC-MS (ES+): 1.9 min, 567 [M + 1] | 4-Chloro-N-(2,5-difluoro-phenyl)-N-[1-(4-methyl-5-{[2-(5-methyl-4H-[1,2,4]triazol-3-yl)-ethylamino]-methyl}-thiazol-2-yl)-ethyl]-benzenesulfonamide |

-continued

| Example | MS | Name |
|---|---|---|
| 47 | LC-MS (ES+): 2.2 min, 569 [M + 1] | 4-Chloro-N-(2,5-difluoro-phenyl)-N-[1-(4-methyl-5-{[(4-methyl-thiazol-2-ylmethyl)-amino]-methyl}-thiazol-2-yl)-ethyl]-benzenesulfonamide |
| 48 | LC-MS (ES+): 2.2 min, 550 [M + 1] | 4-Chloro-N-(2,5-difluoro-phenyl)-N-[1-(4-methyl-5-{[(pyrimidin-4-ylmethyl)-amino]-methyl}-thiazol-2-yl)-ethyl]-benzenesulfonamide |
| 49 | LC-MS (ES+): 1.9 min, 553 [M + 1] | 4-Chloro-N-(2,5-difluoro-phenyl)-N-[1-(4-methyl-5-{[(5-methyl-4H-[1,2,4]triazol-3-ylmethyl)-amino]-methyl}-thiazol-2-yl)-ethyl]-benzenesulfonamide |
| 50 | LC-MS (ES+): 2.1 min, 544 [M + 1] | 4-Chloro-N-(2,5-difluoro-phenyl)-N-(1-{5-[(2-methoxy-2-methyl-propylamino)-methyl]-4-methyl-thiazol-2-yl}-ethyl)-benzenesulfonamide |

Example 51

3-(2-{1-[(4-Chloro-benzenesulfonyl)-(2,5-difluoro-phenyl)-amino]-ethyl}-4-methyl-thiazol-5-yl)-propionic acid methyl ester To a stirred suspension of NaH (60% in mineral oil, 52 mg, 1.3 mmol) in THF (10 mL) under $N_2$ at 0° C. was added methyl diethylphosphonoacetate (238 uL, 1.3 mmol). The mixture was stirred for 15 min, then 4-chloro-N-(2,5-difluoro-phenyl)-N-[1-(5-formyl-4-methyl-thiazol-2-yl)-ethyl]-benzenesulfonamide (0.5 g, 1.1 mmol) in THF (4 mL) was added. The reaction mixture was gradually warmed to room temperature and stirred for 2 h. The reaction was quenched with sat. $NH_4Cl$ aqueous solution and was then diluted with $Et_2O$. The mixture was washed with water, brine and dried with sodium sulfate. The solvent was removed in vacuo and the residue was purified using 10-70% EtOAc in hexane to give 350 mg of 3-(2-{1-[(4-chloro-benzenesulfonyl)-(2,5-difluoro-phenyl)-amino]-ethyl}-4-methyl-thiazol-5-yl)-acrylic acid methyl ester. LC-MS (ES$^+$): 513 [M+1], retention time 2.6 min. 3-(2-{1-[(4-Chloro-benzenesulfonyl)-(2,5-difluoro-phenyl)-amino]-ethyl}-4-methyl-thiazol-5-yl)-acrylic acid methyl ester (300 mg, 0.58 mmol) was dissolved in MeOH (5 mL) and the solution was then cooled to 0° C. under $N_2$. $NiCl_2.6H_2O$ (237 mg, 0.99 mmol) was added and the mixture was stirred for 30 min and $NaBH_4$ (88 mg, 2.3 mmol) was then added. The reaction mixture was stirred at 0° C. for 1 h and then gradually warmed to room temperature over 2 h. The reaction mixture was filtered through a pad of celite and washed the cake with $Et_2O$. The filtrate was concentrated in vacuo and the residue was purified with 15-70% EtOAc in hexane to give 150 mg colorless oil as product. LC-MS (ES$^+$): 515 [M+1], retention time 2.9 min.

Example 52

3-(2-{1-[(4-Chloro-benzenesulfonyl)-(2,5-difluoro-phenyl)-amino]-ethyl}-4-methyl-thiazol-5-yl)-propionic Acid To a stirred solution of 3-(2-{1-[(4-chloro-benzenesulfonyl)-(2,5-difluoro-phenyl)-amino]-ethyl}-4-methyl-thiazol-5-yl)-propionic acid methyl ester (150 mg, 0.29 mmol) in THF (3 mL) and water (3 mL) at room temperature was added LiOH (350 mg, 1.5 mmol). The reaction mixture was stirred for 16 h. No starting material was left. The reaction mixture was adjusted to PH=1 with 1N HCl aqueous solution and extracted with EtOAc. The organic layer was then dried with sodium sulfate and the solvent was removed in vacuo to give 138 mg of colorless oil as product. LC-MS (ES+): 501, retention time 2.7 min.

Intermediate 9: 1-Thiazol-5-yl-ethanol

To a stirred suspension of thiazole (10 g, 117.5 mmol) in THF (300 mL) under $N_2$ at −78° C. was added n-BuLi (2.5 M in hexane, 47 mL, 118.3 mmol) dropwise. After the addition was complete, the mixture was stirred at −78° C. for 30 min, then TBSCI (17.64 g, 117.5 mmol) in THF (40 mL) was added. The reaction mixture was further stirred at −78° C. for 1 h and then gradually warmed to room temperature and stirred for overnight. The reaction was quenched with sat. $NH_4Cl$ aqueous solution and diluted with $Et_2O$ (700 mL). The mixture was washed with water, brine and dried with sodium sulfate. The solvent was removed in vacuo and the residue was then diluted with 2:1 hexane: $Et_2O$ (100 mL) and filtered through a pad of silica gel (eluent 2:1 hexane: $Et_2O$). The filtrate was concentrated in vacuo to give 21.4 g 1-t-butyl-dimethylsilyl thiazole.

The 1-tert-Butyl-dimethylsilyl thiazole compound was diluted with THF (200 mL) and cooled down to −78° C. under $N_2$. To this solution was added n-BuLi (2.5 M in hexane, 47 mL, 118.3 mmol) dropwise. After the addition was complete, the mixture was stirred at −78° C. for 30 min, then acetaldehyde (6.64 mL, 118.3 mmol) was added. The reaction mixture was further stirred at −78° C. for 1 h and then gradually warmed to room temperature and stirred for overnight. The reaction was quenched with $H_2O$ (20 mL) and diluted with $Et_2O$ (600 mL). The mixture was washed with water, brine and dried with sodium sulfate. The solvent was removed in vacuo to give a crude residue. The residue was dissolved in THF (200 mL) and TBAF (1M in THF, 108 mL) was added dropwise at room temperature. The mixture was stirred for 1 h and was then diluted with diluted with $Et_2O$ (600 mL). The mixture was washed with water, brine and dried with sodium sulfate. The solvent was removed in vacuo and the residue was purified with 50-86% EtOAc in hexane to give 4.1 g brown oil as product. 1H-NMR (CDCl$_3$, 400 MHz) δ (ppM): 8.72 (s, 1H), 7.74 (s, 1H), 5.21 (quartet, 1H, J=6.2 Hz), 1.60 (d, 3H, J=6.2 Hz).

Example 53

4-Chloro-N-(2,5-difluoro-phenyl)-N-(1-thiazol-5-yl-ethyl)-benzenesulfonamide

To a stirred solution of triphenylphosphine (5.35 g, 20.4 mmol) in toluene (100 mL) under $N_2$ at room temperature was added 4-chloro-N-(2,5-difluoro-phenyl) benzenesulfonamide (5.2 g, 17.0 mmol), followed by slow addition of di-tert-butyl aza dicarboxylate (4.70 g, 20.4 mmol). After the addition was complete, a solution of 1-thiazol-5-yl-ethanol (2.19 g, 17.0 mmol) in toluene (20 mL) was added dropwise. The reaction mixture was stirred for 16 h and was then diluted with EtOAc. The solution was washed with water, brine and dried with sodium sulfate. The solvent was removed in vacuo and the residue was purified with hexane/EtOAc (4:1) to give 3.5 g of white solid as product. LC-MS (ES+): 415, retention time 2.6 min.

Example 54

4-Chloro-N-(2,5-difluoro-phenyl)-N-[1-(2-formyl-thiazol-5-yl)-ethyl]Benzenesulfonamide To a stirred solution of 4-chloro-N-(2,5-difluoro-phenyl)-N-(1-thiazol-5-yl-ethyl)-benzenesulfonamide (0.5 g, 1.2 mmol) in $Et_2O$ (5 mL) under $N_2$ at −78° C. was added n-BuLi (2.5 M in hexane, 0.58 mL, 1.44 mmol). The mixture was stirred at −78° C. for 30 min, then N-formylmorpholine (166 mg, 1.44 mmol) was added dropwise. The reaction mixture was stirred at −78° C. for 30 min and then at room temperature for 2.5 h. The reaction mixture was diluted with $Et_2O$ (100 mL) and was washed with water, brine and dried with sodium sulfate. The solvent was removed in vacuo and the residue was purified with 20-50% EtOAc in hexane to give 115 mg of white solid as product. LC-MS (ES+): 443, retention time 2.7 min.

Example 55

5-{1-[(4-Chloro-benzenesulfonyl)-(2,5-difluoro-phenyl)-amino]-ethyl}-thiazole-2-carboxylic Acid To a stirred solution of 4-chloro-N-(2,5-difluoro-phenyl)-N-[1-(2-formyl-thiazol-5-yl)-ethyl]benzenesulfonamide (111 mg, 0.25 mmol) in t-BuOH (2 mL) and $H_2O$ (1 mL) under $N_2$ at room temperature was added 2-methyl-2-butene (0.25 mL), $NaClO_2$ (141 mg, 1.25 mmol) and $NaH_2PO_4.H_2O$ (284 mg, 2.0 mmol). The mixture was stirred at room temperature for 2 h and the reaction mixture was diluted with EtOAc (100 mL) and washed with water, brine and dried with sodium sulfate. The solvent was removed in vacuo to give 56 mg of white solid as product. LC-MS (ES+): 459, retention time 2.2 min.

Followed the same procedure in example 51, from 4-Chloro-N-(2,5-difluoro-phenyl)-N-[1-(2-formyl-thiazol-5-yl)-ethyl]benzenesulfonamide the following example was synthesized:

Example 56

3-(5-{1-[(4-Chloro-benzenesulfonyl)-(2,5-difluoro-phenyl)-amino]-ethyl}-thiazol-2-yl)-propionic Acid Methyl Ester LC-MS (ES+): 501, retention time 2.8 min.

Followed the same procedure in example 52, from 3-(5-{1-[(4-Chloro-benzenesulfonyl)-(2,5-difluoro-phenyl)-amino]-ethyl}-thiazol-2-yl)-propionic acid methyl ester the following example was synthesized:

Example 57

3-(5-{1-[(4-Chloro-benzenesulfonyl)-(2,5-difluoro-phenyl)-amino]-ethyl}-thiazol-2-yl)-propionic Acid LC-MS (ES+): 487, retention time 2.5 min.

Example 58

5-{1-[(4-Chloro-benzenesulfonyl)-(2,5-difluoro-phenyl)-amino]-ethyl}-thiazole-2-carboxylic Acid Amide To a stirred solution of 5-{1-[(4-chloro-benzenesulfonyl)-(2,5-difluoro-phenyl)-amino]-ethyl}-thiazole-2-carboxylic acid (280 mg, 0.61 mmol) in THF (12 mL) under $N_2$ at 0° C. was added N-methylmorpholine (80 uL, 0.73 mmol), iso-butylchloroformate (96 uL, 0.73 mmol). After the addition was complete, the reaction mixture was stirred at 0° C. for 1 h and then $NH_4OH$ (128 uL, 0.92 mmol) was added. The mixture was warmed to room temperature and stirred for 16 h. The reaction mixture was diluted with $Et_2O$ (100 mL) and washed with water, brine and dried with sodium sulfate. The solvent was removed in vacuo and the residue was purified with 0-10% MeOH in $CH_2Cl_2$ to give 250 mg solid, which was then triturated with EtOAc to give 133 mg of white solid as product. LC-MS (ES+): 458, retention time 2.5 min.

Followed the same procedure in example 58, from 3-(5-{1-[(4-Chloro-benzenesulfonyl)-(2,5-difluoro-phenyl)-amino]-ethyl}-thiazol-2-yl)-propionic acid the following examples were synthesized:

Example 59

3-(5-{1-[(4-Chloro-benzenesulfonyl)-(2,5-difluoro-phenyl)-amino]-ethyl}-thiazol-2-yl)-propionamide LC-MS (ES+): 486, retention time 2.3 min.

Example 60

3-(5-{1-[(4-Chloro-benzenesulfonyl)-(2,5-difluoro-phenyl)-amino]-ethyl}-thiazol-2-yl)-N-methyl-propionamide LC-MS (ES+): 500, retention time 2.3 min.

Followed the same procedure in example 28, from 4-chloro-N-(2,5-difluoro-phenyl)-N-[1-(2-formyl-thiazol-5-yl)-ethyl]benzenesulfonamide the following examples were synthesized:

| Example | MS | Name |
|---|---|---|
| 61 | LC-MS (ES+): 1.9 min, 528 [M + 1] | 4-Chloro-N-(2,5-difluoro-phenyl)-N-{1-[2-(4-hydroxy-piperidin-1-ylmethyl)-thiazol-5-yl]-ethyl}-benzenesulfonamide |
| 62 | LC-MS (ES+): 2.0 min, 555 [M + 1] | 1-(5-{1-[(4-Chloro-benzenesulfonyl)-(2,5-difluoro-phenyl)-amino]-ethyl}-thiazol-2-ylmethyl)-piperidine-3-carboxylic acid amide |

Example 63

4-Chloro-N-(2,5-difluoro-phenyl)-N-[1-(2-hydroxymethyl-thiazol-5-yl)-ethyl]-benzenesulfonamide.

Isolated as side product from the reactions above. LC-MS (ES+): 445, retention time 2.4 min.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:
1. A compound of the Formula I:

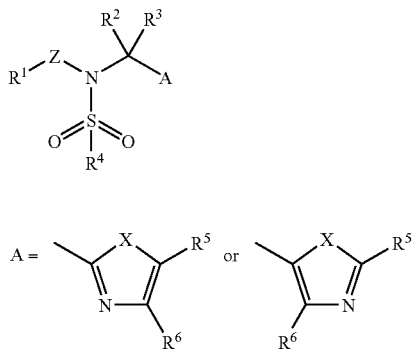

wherein:
- $R^1$ is $(C_6\text{-}C_{14})$ aryl, or -(5-14 membered) heteroaryl, wherein said aryl and heteroaryl are each optionally substituted with one or more $(C_0\text{-}C_4$ alkylene$)\text{-}R^{13}$;
- $R^2$ and $R^3$ are independently selected from the group consisting of: —H, a straight or branched $C_1\text{-}C_6$ alkyl, $C_2\text{-}C_6$ alkenyl, $C_2\text{-}C_6$ alkynyl, $C_3\text{-}C_8$ cycloalkyl, $C_6\text{-}C_{14}$ aryl and (5-14 membered) heteroaryl, wherein said alkyl, alkenyl and alkynyl are each optionally substituted with one or more substituents selected from the group consisting of —F, —Cl, —Br, —OH, $C_1\text{-}C_4$ alkoxy, and —S-($C_1\text{-}C_4$)alkyl, and wherein said aryl and heteroaryl are each optionally substituted with one or more $(C_0\text{-}C_4$ alkylene$)\text{-}R^{13}$; or $R^2$ and $R^3$ taken together form a $C_3\text{-}C_8$ cycloalkyl;
- $R^4$ is $C_6\text{-}C_{14}$ aryl or (5-14 membered) heteroaryl substituted with one or more $(C_0\text{-}C_4$ alkylene$)\text{-}R^{13}$;
- $R^5$ and $R^6$ are independently selected from the group consisting of: —H, —F, —Cl, —Br, —CN, —CHO, —NO$_2$, —C(=O)NR$^9$R$^{10}$, —C(=O)OR$^{10}$, —NR$^9$R$^{10}$, —NR$^9$C(=O)R$^{10}$, —NR$^9$C(=O)OR$^{10}$, and NR$^9$C(=O)NR$^9$R$^{10}$;
- or $R^5$ and $R^6$ are independently a straight or branched $C_1\text{-}C_{20}$ alkyl, $C_2\text{-}C_{20}$ alkenyl, $C_2\text{-}C_{20}$ alkynyl, $(C_0\text{-}C_6$ alkylene)-$(C_3\text{-}C_{12}$ cycloalkyl), or $(C_0\text{-}C_6$ alkylene)-$(C_3\text{-}C_{12}$ heterocycloalkyl), wherein said alkyl, alkenyl, alkynyl, alkylene, cycloalkyl and heteroalkyl are each optionally substituted with one or more $(C_0\text{-}C_6$ alkylene)-$R^7$; or $R^5$ and $R^6$ are independently $(C_0\text{-}C_6$ alkylene)-$(C_6\text{-}C_{14}$ aryl) or $(C_0\text{-}C_6$ alkylene)-(5-14 membered heteroaryl), wherein said aryl and heteroaryl are each optionally substituted with one or more $R^7$ and wherein said alkylene is optionally substituted with one or more $(C_0\text{-}C_6$ alkylene)-$R^8$; or $R^5$ and $R^6$, when attached to the adjacent carbon atoms of the thiazole ring, together form a (4-8 membered) cycloalkyl, (4-8 membered)-heterocycloalkyl, or $C_6\text{-}C_{10}$ aryl wherein said cycloalkyl and heteroalkyl are each substituted with one or more $(C_0\text{-}C_6$ alkylene)-$R^8$, $(C_0\text{-}C_6$ alkylene)-$(C_6\text{-}C_{14}$ aryl), and $(C_0\text{-}C_6$ alkylene)-(5-14 membered heteroaryl), wherein said aryl and heteroaryl are each optionally substituted with one or more $R^7$;
- Z is a bond or a straight or branched $C_1\text{-}C_6$ alkylene, wherein each hydrogen atom of said alkylene is optionally independently replaced with a fluorine;
- X is O or S;
- $R^7$ is —F, —Cl, —Br, —OH, —CN, —CHO, —NO$_2$, —NR$^9$R$^{10}$, —NR$^9$C(=O)R$^{10}$, —NR$^9$C(=O)NR$^9$R$^{10}$, —NR$^9$C(=O)OR$^{10}$, —OC(=O)—R$^9$, —OC(=O)NR$^9$R$^{10}$, —C(=O)NR$^9$R$^{10}$, —C(=O)OR$^{10}$, —SO$_2$NR$^9$R$^{10}$, —C$_1$-C$_6$ alkyl, —C$_2$-C$_6$ alkenyl, —C$_2$-C$_6$ alkynyl —C$_3$-C$_8$ cycloalkyl, —C$_3$-C$_8$ heterocycloalkyl, —C$_1$-C$_6$ alkoxy, -(C$_6$-C$_{14}$) aryloxy, -(5-14 membered) heteroaryloxy, -(C$_0$-C$_4$ alkylene)-(C$_6$-C$_{14}$) aryl, or
- -(C$_0$-C$_4$ alkylene)-(5-14 membered) heteroaryl, wherein said alkyl, alkenyl, alkynyl, cycloalkyl and heterocycloalkyl are each optionally substituted with one or more R$_8$, and wherein each hydrogen atom of said alkyl, alkenyl, alkynyl, cycloalkyl, heterocycloalkyl and alkoxy is optionally independently replaced with a fluorine;
- $R^8$ is —F, —Cl, —Br, —CN, —CHO, —OR$^9$, —OC(=O)—R$^9$, —OC(=O)NR$^9$R$^{10}$, —NO$_2$, —NR$^9$R$^{10}$, —NR$^9$C(=O)R$^{10}$, —NR$^9$C(=O)NR$^9$R$^{10}$, —NR$^9$C(=O)OR$^{10}$, —C(=O)NR$^9$R$^{10}$, —SO$_2$NR$^9$R$^{10}$, —C(=O)R$^{10}$, or —C(=O)OR$^{10}$;
- $R^9$ and $R^{10}$ are —H, —C$_1$-C$_6$ alkyl, —C$_2$-C$_6$ alkenyl, —C$_2$-C$_6$ alkynyl, -(C$_0$-C$_4$ alkylene)-(C$_3$-C$_8$ cycloalkyl), -(C$_0$-C$_4$ alkylene)-(C$_6$-C$_{14}$ aryl), -(C$_0$-C$_4$ alkylene)-(3-8 membered heterocycloalkyl), or -(C$_0$-C$_4$ alkylene)-(5-14 membered heteroaryl), wherein said alky, alkenyl, alkynyl, cycloalkyl, aryl, heterocycloalkyl, and heteroaryl are each optionally independently substituted with one or more substituents independently selected from the group consisting of —F, —Cl, —Br, —CN, —CHO, —OH, —NO$_2$, —NR$^{11}$R$^{12}$, —C(=)ONR$^{11}$R$^{12}$, —C(=O)R$^{11}$, —C(=O)OR$^{12}$, —SO$_2$NR$^{11}$R$^{12}$, —C$_1$-C$_6$ alkyl, —C$_1$-C$_6$ alkoxy, —C$_1$-C$_6$ hydroxyalkyl, -(C$_0$-C$_4$)-(C$_6$-C$_{14}$) aryl), and -(C$_0$-C$_4$)-(5-14 membered heteroaryl);
- or $R^9$ and $R^{10}$ with nitrogen forms a 4-8 membered heterocycloalkyl moiety, wherein said heterocycloalkyl is optionally substituted with one or more substitutents selected from the group consisting of —F, —Cl, —Br, —CN, —CHO, —OH, —NO$_2$, —NR$^{11}$R$^{12}$, —C(=)ONR$^{11}$R$^{12}$, —C(=O)R$^{11}$, —C(=O)OR$^{12}$, —SO$_2$NR$^{11}$R$^{12}$, -C$_1$-C$_6$ alkyl, -C$_2$-C$_6$ alkenyl, —C$_2$-C$_6$ alkynyl, —C$_1$-C$_6$ alkoxy, —C$_3$-C$_8$ cycloalkyl, C$_3$-C$_8$ heterocycloalkyl, C$_6$-C$_{10}$ aryl, and 5-14 membered heteroaryl, wherein said alkyl, alkenyl, alkynyl, alkoxy, cycloalkyl, heterocycloalkyl, aryl, heteroaryl are each optionally substituted with F, —Cl, —Br, —CN, —OR$^{11}$, —OC(=O)—R$^{11}$, —OC(=O)NR$^{11}$R$^{12}$, —NO$_2$, —NR$^{11}$R$^{12}$, —NR$^{11}$C(=O)R$^{12}$, —NR$^{11}$C(=O)NR$^{11}$R$^{12}$, —NR$^{11}$C(=O)OR$^{12}$, —C(=O)NR$^{11}$R$^{12}$, —SO$_2$NR$^{11}$R$^{12}$,
- —C(=O)R$^{11}$, or —C(=O)OR$^{11}$;
- $R^{11}$ and $R^{12}$ are hydrogen, C$_1$-C$_6$ alkyl, C$_2$-C$_6$ alkenyl, C$_2$-C$_6$ alkynyl, C$_3$-C$_8$ cycloalkyl, 4-8 membered heterocycloalkyl, C$_6$-C$_{14}$ aryl or 5-14 membered heteroaryl, wherein said alkyl, alkenyl, alkynyl, aryl and heteroaryl are each optionally independently substituted with from one to three substituents independently selected from the group consisting of —OH, —C$_1$-C$_6$ alkyl,
- —C$_2$-C$_6$ alkenyl, —C$_2$-C$_6$ alkynyl, —C$_1$-C$_6$ alkoxy, —C$_2$-C$_6$ alkenoxy, —C$_2$-C$_6$ alkynoxy, —C$_1$-C$_6$ hydroxyalkyl, —F, —Cl, —Br, —I, —CN, —NO$_2$, —CF$_3$, —NH$_2$, —NH(C$_1$-C$_6$ alkyl), —N(C$_1$-C$_6$ alkyl)$_2$, —C(=O)NH$_2$, —C(=O)NH(C$_1$-C$_6$ alkyl), —C(=O)N(C$_1$-C$_6$ alkyl)$_2$, —SO$_2$NH$_2$, —SO$_2$NH(C$_1$-C$_6$ alkyl), —SO$_2$N(C$_1$-C$_6$ alkyl)$_2$, —C(=O)H, —C(=O)OH and —C(=O)O(C$_1$-C$_6$ alkyl), wherein said alkyl, alkenyl and alkynyl substituents are each optionally independently further substituted with from one to six fluorine atoms;

or $R^{11}$ and $R^{12}$ with nitrogen taken together form a 4-8 membered heterocycloalkyl, wherein said heterocycloalkyl is optionally independently substituted with from one to three substituents independently selected from the group consisting of —OH, —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —$NO_2$, —$CF_3$, —$NH_2$, —NH($C_1$-$C_6$ alkyl), —N($C_1$-$C_6$ alkyl)$_2$, —C(=O)$NH_2$, —C(=O)NH($C_1$-$C_6$ alkyl), —C(=O)N($C_1$-$C_6$ alkyl)$_2$, —$SO_2N$ $H_2$, —$SO_2NH(C_1$-$C_6$ alkyl), —$SO_2N(C_1$-$C_6$ alkyl)$_2$, —C(=O)H, —C(=O)OH and —C(=O)O($C_1$-$C_6$ alkyl), wherein said alkyl, alkenyl and alkynyl substituents are each optionally independently further substituted with from one to six fluorine atoms; and $R^{13}$ is —F, —Cl, —Br, —CN, —CHO, —OH, —$NO_2$, —$NR^{11}R^{12}$, —C(=)O$NR^{11}R^{12}$, —C(=O)$R^{11}$, —C(=O)$OR^{12}$, —$SO_2NR^{11}R^{12}$, —$C_1$-$C_6$ alkyl, —$C_1$-$C_6$ alkoxy, —$C_3$-$C_8$ cycloalkyl, 4-8 membered heterocycloalkyl, $C_6$-$C_{10}$ aryl or 5-14 membered heteroaryl, wherein each hydrogen atom of said alkyl, alkoxy, cycloalkyl and heterocycloalkyl is optionally independently replaced with a fluorine.

2. A compound according to claim 1, wherein Z is a bond.

3. A compound according to claim 1, wherein Z is methylene.

4. A compound according to claim 1, wherein $R^2$ is hydrogen and $R^3$ is independently selected from the group consisting of —H, a straight or branched $C_1$-$C_6$ alkyl, $C_2$-$C_6$ alkenyl, $C_2$-$C_6$ alkynyl, $C_6$-$C_{14}$ aryl and (5-14 membered) heteroaryl.

5. A compound of Formula I according to claim 1, wherein X is S.

6. A compound of Formula I according to claim 5, wherein

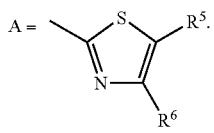

7. A compound of Formula I according to claim 5, wherein

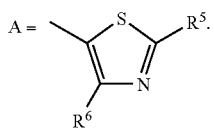

8. A compound according to claim 4, wherein $R^6$ is —H, —F, —Cl, —CN, —CHO, a straight or branched $C_1$-$C_{10}$ alkyl, $C_2$-$C_{10}$ alkenyl, $C_2$-$C_{10}$ alkynyl, ($C_0$-$C_6$ alkylene)-($C_3$-$C_{12}$ cycloalkyl), ($C_0$-$C_6$ alkylene)-($C_3$-$C_{12}$ heterocycloalkyl), ($C_0$-$C_6$ alkylene)-($C_6$-$C_{14}$ aryl) or ($C_0$-$C_6$ alkylene)-(5-14 membered heteroaryl), wherein said alkyl, alkenyl, alkynyl, alkylene, cycloalkyl and heteroalkyl are each optionally substituted with one or more ($C_0$-$C_6$ alkylene)-$R^7$; and wherein said aryl and heteroaryl are each optionally substituted with one or more $R^7$.

9. A compound according to claim 8, wherein $R^5$ is independently selected from the group consisting of: —H, —F, —Cl, —Br, —CN, —CHO, —$NO_2$, —C(=O)$NR^9R^{10}$, —C(=O)$OR^{10}$, —$NR^9R^{10}$, —$NR^9C$(=O)$R^{10}$, —$NR^9C$(=O)$OR^{10}$, and $NR^9C$(=O)$NR^9R^{10}$; or $R^5$ is straight or branched $C_1$-$C_{20}$ alkyl, $C_2$-$C_{20}$ alkenyl, $C_2$-$C_{20}$ alkynyl, ($C_0$-$C_6$ alkylene)-($C_3$-$C_{12}$ cycloalkyl), or ($C_0$-$C_6$ alkylene)-($C_3$-$C_{12}$ heterocycloalkyl), wherein said alkyl, alkenyl, alkynyl, alkylene, cycloalkyl and heteroalkyl are each optionally substituted with one or more ($C_0$-$C_6$ alkylene)-$R^7$; or $R^5$ is ($C_0$-$C_6$ alkylene)-($C_6$-$C_{14}$ aryl) or ($C_0$-$C_6$ alkylene)-(5-14 membered heteroaryl), wherein said aryl and heteroaryl are each optionally substituted with one or more $R^7$ and wherein said alkylene is optionally substituted with one or more ($C_0$-$C_6$ alkylene)-$R^8$.

10. A compound according to claim 5, wherein $R^5$ and $R^6$ taken together form a (4-8 membered) cycloalkyl, (4-8 membered) heterocycloalkyl, or $C_6$-$C_{10}$ aryl wherein said cycloalkyl and heteroalkyl are each substituted with one or more ($C_0$-$C_6$ alkylene)-$R_8$, ($C_0$-$C_6$ alkylene)-($C_6$-$C_{14}$ aryl), and ($C_0$-$C_6$ alkylene)-(5-14 membered heteroaryl), and wherein said aryl and heteroaryl are each optionally substituted with one or more $R^7$.

11. A compound according to claim 4, wherein $R^2$ is hydrogen and $R^3$ is methyl.

12. A compound according to claim 8, wherein $R^6$ is hydrogen, —F, —CN or -($C_1$-$C_4$) alkyl.

13. A compound according to claim 1 selected from the group consisting of:

3-(2-{1-[(4-Chloro-benzenesulfonyl)-(2,5-difluoro-phenyl)-amino]-ethyl}-thiazol-5-yl)-propionic acidmethyl ester;

3-(2-{1-[(4-Chloro-benzenesulfonyl)-(2,5-difluoro-phenyl)-amino]-ethyl}-thiazol-5-yl)-propionic acid;

4-Chloro-N-(2,5-difluoro-phenyl)-N-{1-[5-(3-morpholin-4-yl-3-oxo-propyl]-thiazol-2-yl]-ethyl}-benzenesulfonamide;

4-Chloro-N-(2,5-difluoro-phenyl)-N-(1-{5-[3-(4-hydroxy-piperidin-1-yl)-3-oxo-propyl]-thiazol-2-yl}-ethyl)-benzenesulfonamide;

1-[3-(2-{1-[(4-Chloro-benzenesulfonyl)-(2,5-difluorophenyl)-amino]-ethyl}-thiazol-5-yl)-propionyl]-piperidine-3-carboxylic acid diethylamide;

4-Chloro-N-(2,5-difluoro-phenyl)-N-(1-{5-[3-oxo-3-(4-phenethyl-piperazin-1-yl)-propyl]-thiazol-2-yl}-ethyl)-benzenesulfonamide;

N-tert-Butyl-3-(2-{1-[(4-chloro-benzenesulfonyl)-(2,5-difluoro-phenyl)-amino]-ethyl}-thiazol-5-yl)-propionamide;

4-Chloro-N-(2,5-difluoro-phenyl)-N-{1-[5-(3-oxo-3-pyrrolidin-1-yl-propyl)-thiazol-2-yl]-ethyl}-benzenesulfonamide;

4-Chloro-N-(2,5-difluoro-phenyl)-N-(1-{5-[3-(3-hydroxymethyl-piperidin-1-yl)-3-oxo-propyl]-thiazol-2-yl}-ethyl)-benzenesulfonamide;

3-(2-{1-[(4-Chloro-benzenesulfonyl)-(2,5-difluoro-phenyl)-amino]-ethyl}-thiazol-5-yl)-propionamide;

3-(2-{1-[(4-Chloro-benzenesulfonyl)-(2,5-difluoro-phenyl)-amino]-ethyl}-thiazol-5-yl)-N-(1-ethyl-propyl)-propionamide;

3-(2-{1-[(4-Chloro-benzenesulfonyl)-(2,5-difluoro-phenyl)-amino]-ethyl}-thiazol-5-yl)-N-(3,3-dimethyl-butyl)-propionamide;

4-Chloro-N-(2,5-difluoro-phenyl)-N-{1-[5-(3-hydroxy-3-methyl-butyl)-thiazol-2-yl]-ethyl}-benzenesulfonamide;

4-Chloro-N-(2,5-difluoro-phenyl)-N-{1-[5-(3-hydroxy-propyl)-thiazol-2-yl]-ethyl}-benzenesulfonamide;

4-Chloro-N-(2,5-difluoro-phenyl)-N-{1-[5-(3-oxo-propyl)-thiazol-2-yl]-ethyl}-benzenesulfonamide;
4-Chloro-N-(2,5-difluoro-phenyl)-N-{1-[5-(2-hydroxy-ethyl)-4-methyl-thiazol-2-yl]-ethyl}-benzenesulfonamide;.
4-Chloro-N-(2,5-difluoro-phenyl)-N-{1-[5-(2-hydroxy-ethyl)-4-methyl-thiazol-2-yl]-propyl}-benzenesulfonamide;
4-Chloro-N-(2,5-difluoro-phenyl)-N-{1-[5-(2-hydroxy-ethyl)-4-methyl-thiazol-2-yl]-3-methyl-butyl}-benzenesulfonamide;
4-Chloro-N-(2,5-difluoro-phenyl)-N-[5-(2-hydroxy-ethyl)-4-methyl-thiazol-2-ylmethyl]-benzenesulfonamide;
4-Chloro-N-(2,5-difluoro-phenyl)-N-{[5-(2-hydroxy-ethyl)-4-methyl-thiazol-2-yl]-phenyl-methyl}-benzenesulfonamide;
N-(1-Benzothiazol-2-yl-ethyl)-4-chloro-N-(2,5-difluoro-phenyl)-benzenesulfonamide;
N-(1-Benzothiazol-2-yl-ethyl)-4-chloro-N-(2,5-difluoro-phenyl)-benzenesulfonamide;
4-Chloro-N-(2,5-difluoro-phenyl)-N-[1-(5-trifluoromethyl-benzothiazol-2-yl)-ethyl]-benzenesulfonamide;
4-Chloro-N-(2,5-difluoro-phenyl)-N-[1-(5-phenyl-thiazol-2-yl)-ethyl]-benzenesulfonamide;
4-Chloro-N-(2,5-difluoro-phenyl)-N-(1-thiazol-2-yl-ethyl)-benzenesulfonamide;
4-Chloro-N-(2,5-difluoro-phenyl)-N-[1-(4-methyl-5-vinyl-thiazol-2-yl)-ethyl]-benzenesulfonamide;
4-Chloro-N-(2,5-difluoro-phenyl)-N-[1-(5-formyl-4-methyl-thiazol-2-yl)-ethyl]-benzenesulfonamide;
4-Chloro-N-(2,5-difluoro-phenyl)-N-{1-[4-methyl-5-(4-methyl-piperazin-1-ylmethyl)-thiazol-2-yl]-ethyl}-benzenesulfonamide;
4-Chloro-N-(2,5-difluoro-phenyl)-N-{1-[5-(4-hydroxy-piperidin-1-ylmethyl)-4-methyl-thiazol-2-yl]-ethyl}-benzenesulfonamide;
2-(R)-[(2-{1-[(4-Chloro benzenesulfonyl)-(2,5-difluoro-phenyl)-amino]-ethyl}-4-methyl-thiazol-5-ylmethyl)-amino]-4-methyl-pentanoic acid amide;
4-Chloro-N-(2,5-difluoro-phenyl)-N-(1-{5-[(3-methoxy-propylamino)-methyl]-4-methyl-thiazol-2-yl}-ethyl)-benzenesulfonamide;
4-Chloro-N-(2,5-difluoro-phenyl)-N-[1-(4-methyl-5-piperidin-1-ylmethyl-thiazol-2-yl)-ethyl]-benzenesulfonamide;
4-Chloro-N-(2,5-difluoro-phenyl)-N-[1-(4-methyl-5-{[3-(2-oxo-pyrrolidin-1-yl)-propylamino]-methyl}-thiazol-2-yl)-ethyl]-benzenesulfonamide;
4-Chloro-N-(2,5-difluoro-phenyl)-N-(1-{4-methyl-5-[(2-pyridin-2-yl-ethylamino)-methyl]-thiazol-2-yl}-ethyl)-benzenesulfonamide;
4-Chloro-N-(2,5-difluoro-phenyl)-N-(1-{4-methyl-5-[(2-phenoxy-ethylamino)-methyl]-thiazol-2-yl}-ethyl)-benzenesulfonamide;
4-Chloro-N-(2,5-difluoro-phenyl)-N-(1-{5-[(5-hydroxy-1,5-dimethyl-hexylamino)-methyl]-4-methyl-thiazol-2-yl}-ethyl)-benzenesulfonamide;
N-{1-[5-(4-Acetyl-piperazin-1-ylmethyl)-4-methyl-thiazol-2-yl]-ethyl}-4-chloro-N-(2,5-difluoro-phenyl)-benzenesulfonamide;
1-(2-{1-[(4-Chloro-benzenesulfonyl)-(2,5-difluoro-phenyl)-amino]-ethyl}-4-methyl-thiazol-5-ylmethyl)-piperidine-4-carboxylic acid amide;
2-[(2-{1-[(4-Chloro-benzenesulfonyl)-(2,5-difluoro-phenyl)-amino]-ethyl}-4-methyl-thiazol-5-ylmethyl)-methyl-amino]-acetamide;
4-Chloro-N-(2,5-difluoro-phenyl)-N-{1-[4-methyl-5-(3-oxo-piperazin-1-ylmethyl)-thiazol-2-yl]-ethyl}-benzenesulfonamide;
4-Chloro-N-(2,5-difluoro-phenyl)-N-{1-[4-methyl-5-(5-oxo-[1,4]diazepan-1-ylmethyl)-thiazol-2-yl]-ethyl}-benzenesulfonamide;
3-[(2-{1-[(4-Chloro-benzenesulfonyl)-(2,5-difluoro-phenyl)-amino]-ethyl}-4-methyl-thiazol-5-ylmethyl)-amino]-propionamide;
2-[(2-{1-[(4-Chloro-benzenesulfonyl)-(2,5-difluoro-phenyl)-amino]-ethyl}-4-methyl-thiazol-5-ylmethyl)-amino]-acetamide;
2-[(2-{1-[(4-Chloro-benzenesulfonyl)-(2,5-difluoro-phenyl)-amino]-ethyl}-4-methyl-thiazol-5-ylmethyl)-amino]-N-methyl-acetamide;
4-Chloro-N-(2,5-difluoro-phenyl)-N-[1-(4-methyl-5-{[2-(2-oxo-pyrrolidin-1-yl)-ethylamino]-methyl}-thiazol-2-yl)-ethyl]-benzenesulfonamide;
4-Chloro-N-(2,5-difluoro-phenyl)-N-[1-(4-methyl-5-{[2-(5-methyl-4H-[1,2,4]triazol-3-yl)-ethylamino]-methyl}-thiazol-2-yl)-ethyl]-benzenesulfonamide;
4-Chloro-N-(2,5-difluoro-phenyl)-N-[1-(4-methyl-5-{[(4-methyl-thiazol-2-ylmethyl)-amino]-methyl}-thiazol-2-yl)-ethyl]-benzenesulfonamide;
4-Chloro-N-(2,5-difluoro-phenyl)-N-[1-(4-methyl-5-{[(pyrimidin-4-ylmethyl)-amino]-methyl}-thiazol-2-yl)-ethyl]-benzenesulfonamide;
4-Chloro-N-(2,5-difluoro-phenyl)-N-[1-(4-methyl-5-{[(5-methyl-4H-[1,2,4]triazol-3-ylmethyl)-amino]-methyl}-thiazol-2-yl)-ethyl]-benzenesulfonamide;
4-Chloro-N-(2,5-difluoro-phenyl)-N-(1-{5-[(2-methoxy-2-methyl-propylamino)-methyl]-4-methyl-thiazol-2-yl}-ethyl)-benzenesulfonamide;
3-(2-{1-[(4-Chloro-benzenesulfonyl)-(2,5-difluoro-phenyl)-amino]-ethyl}-4-methyl-thiazol-5-yl)-propionic acid methyl ester;
3-(2-{1-[(4-Chloro-benzenesulfonyl)-(2,5-difluoro-phenyl)-amino]-ethyl}-4-methyl-thiazol-5-yl)-propionic acid;
4-Chloro-N-(2,5-difluoro-phenyl)-N-(1-thiazol-5-yl-ethyl)-benzenesulfonamide;
4-Chloro-N-(2,5-difluoro-phenyl)-N-[1-(2-formyl-thiazol-5-yl)-ethyl]benzenesulfonamide;
5-{1-[(4-Chloro-benzenesulfonyl)-(2,5-difluoro-phenyl)-amino]-ethyl}-thiazole-2-carboxylic acid;
3-(5-{1-[(4-Chloro-benzenesulfonyl)-(2,5-difluoro-phenyl)-amino]-ethyl}-thiazol-2-yl)-propionic acid methyl ester;
3-(5-{1-[(4-Chloro-benzenesulfonyl)-(2,5-difluoro-phenyl)-amino]-ethyl}-thiazol-2-yl)-propionic acid;
5-{1-[(4-Chloro-benzenesulfonyl)-(2,5-difluoro-phenyl)-amino]-ethyl}-thiazole-2-carboxylic acid amide;
3-(5-{1-[(4-Chloro-benzenesulfonyl)-(2,5-difluoro-phenyl)-amino]-ethyl}-thiazol-2-yl)-propionamide;
3-(5-{1-[(4-Chloro-benzenesulfonyl)-(2,5-difluoro-phenyl)-amino]-ethyl}-thiazol-2-yl)-N-methyl-propionamide;
4-Chloro-N-(2,5-difluoro-phenyl)-N-{1-[2-(4-hydroxy-piperidin-1-ylmethyl)-thiazol-5-yl]-ethyl}-benzenesulfonamide;
1-(5-{1-[(4-Chloro-benzenesulfonyl)-(2,5-difluoro-phenyl)-amino]-ethyl}-thiazol-2-ylmethyl)-piperidine-3-carboxylic acid amide; and
4-Chloro-N-(2,5-difluoro-phenyl)-N-[1-(2-hydroxymethyl-thiazol-5-yl)-ethyl]-benzenesulfonamide;
and pharmaceutically acceptable salts thereof.

* * * * *